(12) United States Patent
Sund et al.

(10) Patent No.: US 10,568,809 B2
(45) Date of Patent: *Feb. 25, 2020

(54) LIQUID-TRANSFER ADAPTER BEVELED SPIKE

(71) Applicant: FERRING B.V., Hoofddorp (NL)

(72) Inventors: Julius C. Sund, Plymouth, MN (US); Kevin D. Swanson, Plymouth, MN (US)

(73) Assignee: FERRING B.V., Hoofddorp (NL)

( * ) Notice: Subject to any disclaimer, the term of this patent is extended or adjusted under 35 U.S.C. 154(b) by 394 days.

This patent is subject to a terminal disclaimer.

(21) Appl. No.: 14/973,789

(22) Filed: Dec. 18, 2015

(65) Prior Publication Data
US 2016/0101021 A1 Apr. 14, 2016

Related U.S. Application Data

(63) Continuation of application No. 13/184,211, filed on Jul. 15, 2011, now Pat. No. 9,220,660.

(51) Int. Cl.
A61J 1/14 (2006.01)
A61J 1/20 (2006.01)
(Continued)

(52) U.S. Cl.
CPC ............. A61J 1/201 (2015.05); A61J 1/1406 (2013.01); A61J 1/2096 (2013.01); A61M 5/20 (2013.01);
(Continued)

(58) Field of Classification Search
CPC .......... A61M 5/20; A61J 1/1406; A61J 1/201; A61J 1/2051; A61J 1/2055; A61J 1/2065; A61J 1/2096; A61J 2200/10
See application file for complete search history.

(56) References Cited

U.S. PATENT DOCUMENTS 547,370 A    10/1895 Chalefou
1,465,793 A   8/1923 Schilling
(Continued)

FOREIGN PATENT DOCUMENTS

AR    00081651    10/2012
AR     082053     11/2012
(Continued)

OTHER PUBLICATIONS

English Translation of Notification of Reasons for Refusal dated Sep. 20, 2016 for Japanese Patent Application No. 2014-520360.
(Continued)

Primary Examiner — Kai H Weng
(74) Attorney, Agent, or Firm — Morgan, Lewis & Bockius LLP

(57) ABSTRACT

A liquid-transfer adapter operatively interposable between an injector and a vial is provided. The adapter has an injector engaging portion configured for fluidly coupling to an injector and a vial coupling. The vial coupling includes a spike that has a spike axis and a tip portion configured for piercing a septum of a vial. The tip portion includes a plurality of facets that meet each other at one or more edges and at least one of the one or more edges is sloped with respect to the spike axis. The spike defines a channel extending therethrough in fluid communication with the injector engaging portion. A channel opening is defined in at least one of the facets and disposed without interrupting the edges.

22 Claims, 15 Drawing Sheets

(51) Int. Cl.
*A61M 5/30* (2006.01)
*A61M 5/20* (2006.01)

(52) U.S. Cl.
CPC .............. *A61M 5/30* (2013.01); *A61J 1/2051* (2015.05); *A61J 1/2055* (2015.05); *A61J 2200/10* (2013.01)

(56) References Cited

U.S. PATENT DOCUMENTS

| | | |
|---|---|---|
| 1,512,294 A | 10/1924 | Marcy |
| 1,687,323 A | 10/1928 | Cook |
| 2,354,649 A | 8/1944 | Bruckner |
| 2,607,344 A | 8/1952 | Brown |
| 2,645,223 A | 7/1953 | Lawshe |
| 2,648,334 A | 8/1953 | Brown |
| 2,687,730 A | 8/1954 | Hein |
| 2,688,967 A | 9/1954 | Huber |
| 2,699,166 A | 1/1955 | Bickinson |
| 2,717,601 A | 9/1955 | Brown |
| 2,728,341 A | 12/1955 | Roehr |
| 2,737,946 A | 3/1956 | Hein, Jr. |
| 2,813,528 A | 11/1957 | Blackman |
| 2,866,458 A | 12/1958 | Mesa et al. |
| 2,888,924 A | 6/1959 | Dunmire |
| 2,893,390 A | 7/1959 | Lockhart |
| 3,130,724 A | 4/1964 | Higgins |
| 3,166,069 A | 1/1965 | Enstrom |
| 3,375,825 A | 4/1968 | Keller |
| 3,382,865 A | 5/1968 | Worrall |
| 3,526,225 A | 9/1970 | Hayamamachi |
| 3,557,784 A | 1/1971 | Shields |
| 3,563,098 A | 2/1971 | Gley |
| 3,605,744 A | 9/1971 | Dwyer |
| 3,688,765 A | 9/1972 | Gasaway |
| 3,702,609 A | 11/1972 | Steiner |
| 3,712,301 A | 1/1973 | Sarnoff |
| 3,742,948 A | 7/1973 | Post et al. |
| 3,770,026 A | 11/1973 | Isenberg |
| 3,790,048 A | 2/1974 | Luciano et al. |
| 3,797,489 A | 3/1974 | Sarnoff |
| 3,797,491 A | 3/1974 | Hurschman |
| 3,811,441 A | 5/1974 | Sarnoff |
| 3,831,814 A | 8/1974 | Butler |
| 3,848,593 A | 11/1974 | Baldwin |
| 3,882,863 A | 5/1975 | Sarnoff et al. |
| 3,892,237 A | 7/1975 | Steiner |
| 3,895,633 A | 7/1975 | Bartner et al. |
| 3,946,732 A | 3/1976 | Hurscham |
| 4,031,893 A | 6/1977 | Kaplan et al. |
| 4,067,333 A | 1/1978 | Reinhardt et al. |
| 4,127,118 A | 11/1978 | Latorre |
| 4,171,698 A | 10/1979 | Genese |
| 4,222,392 A | 9/1980 | Brennan |
| 4,227,528 A | 10/1980 | Wardlaw |
| 4,258,713 A | 3/1981 | Wardlaw |
| 4,282,986 A | 8/1981 | af Ekenstam et al. |
| 4,316,463 A | 2/1982 | Schmitz et al. |
| 4,316,643 A | 2/1982 | Burk et al. |
| 4,328,802 A | 5/1982 | Curley et al. |
| 4,333,456 A | 6/1982 | Webb |
| 4,333,458 A | 6/1982 | Margulies et al. |
| 4,338,980 A | 7/1982 | Schwebel et al. |
| 4,373,526 A | 2/1983 | Kling |
| 4,378,015 A | 3/1983 | Wardlaw |
| 4,411,661 A | 10/1983 | Kersten |
| 4,484,910 A | 11/1984 | Sarnoff et al. |
| 4,529,403 A | 7/1985 | Kamstra |
| 4,553,962 A | 11/1985 | Brunet |
| 4,558,690 A | 12/1985 | Joyce |
| 4,573,971 A | 3/1986 | Kamstra |
| 4,592,745 A | 6/1986 | Rex et al. |
| 4,624,660 A | 11/1986 | Mijers et al. |
| 4,634,027 A | 1/1987 | Kanarvogel |
| 4,661,098 A | 4/1987 | Bekkering et al. |
| 4,662,878 A | 5/1987 | Lindmayer |
| 4,664,653 A | 5/1987 | Sagstetter et al. |
| 4,664,655 A | 5/1987 | Orentreich et al. |
| 4,678,461 A | 7/1987 | Mesa |
| 4,719,825 A | 1/1988 | LaHaye et al. |
| 4,722,728 A | 2/1988 | Dixon |
| 4,774,772 A | 10/1988 | Vetter et al. |
| 4,790,824 A | 12/1988 | Morrow et al. |
| 4,818,517 A | 4/1989 | Kwee et al. |
| 4,820,286 A | 4/1989 | van der Wal |
| 4,822,340 A | 4/1989 | Kamstra |
| 4,830,217 A | 5/1989 | Dufresne et al. |
| 4,874,381 A | 10/1989 | Vetter |
| 4,883,472 A | 11/1989 | Michel |
| 4,913,699 A | 4/1990 | Parsons |
| 4,915,701 A | 4/1990 | Halkyard |
| 4,929,238 A | 5/1990 | Baum |
| 4,936,833 A | 6/1990 | Sams |
| 4,940,460 A | 7/1990 | Casey et al. |
| 4,966,581 A | 10/1990 | Landau |
| 4,968,302 A | 11/1990 | Schluter et al. |
| 4,973,318 A | 11/1990 | Holm et al. |
| 4,976,701 A | 12/1990 | Ejlersen et al. |
| 4,982,769 A | 1/1991 | Fournier et al. |
| 4,986,816 A | 1/1991 | Steiner et al. |
| 5,042,977 A | 8/1991 | Bechtold et al. |
| 5,062,830 A | 11/1991 | Dunlap |
| 5,064,413 A | 11/1991 | McKinnon et al. |
| 5,069,670 A | 12/1991 | Vetter et al. |
| 5,078,680 A | 1/1992 | Sarnoff |
| 5,080,648 A | 1/1992 | D'Antonio |
| 5,080,649 A | 1/1992 | Vetter |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,388 A | 4/1992 | Richmond |
| 5,102,393 A | 4/1992 | Sarnoff et al. |
| 5,104,380 A | 4/1992 | Holman et al. |
| 5,114,406 A | 5/1992 | Gabriel et al. |
| 5,137,516 A | 8/1992 | Rand et al. |
| 5,137,528 A | 8/1992 | Crose |
| 5,139,490 A | 8/1992 | Vetter et al. |
| 5,163,907 A | 11/1992 | Szuszkiewicz |
| 5,176,643 A | 1/1993 | Kramer et al. |
| 5,180,370 A | 1/1993 | Gillespie |
| 5,185,985 A | 2/1993 | Vetter et al. |
| 5,195,983 A | 3/1993 | Boese |
| 5,221,348 A | 6/1993 | Masano |
| 5,226,895 A | 7/1993 | Harris |
| 5,232,459 A | 8/1993 | Hjertman |
| 5,256,142 A | 10/1993 | Colavecchio |
| 5,263,934 A | 11/1993 | Haak |
| 5,271,744 A | 12/1993 | Kramer et al. |
| 5,279,543 A | 1/1994 | Glikfeld et al. |
| 5,279,576 A | 1/1994 | Loo et al. |
| 5,279,585 A | 1/1994 | Balkwill |
| 5,279,586 A | 1/1994 | Balkwill |
| 5,281,198 A | 1/1994 | Haber et al. |
| 5,290,228 A | 3/1994 | Uemura et al. |
| 5,295,965 A | 3/1994 | Wilmot |
| 5,300,030 A | 4/1994 | Crossman et al. |
| 5,304,128 A | 4/1994 | Haber et al. |
| 5,304,152 A | 4/1994 | Sams |
| 5,308,341 A | 5/1994 | Chanoch |
| 5,318,522 A | 6/1994 | D'Antonio |
| 5,320,603 A | 6/1994 | Vetter et al. |
| 5,330,431 A | 7/1994 | Herskowitz |
| 5,332,399 A | 7/1994 | Grabenkort et al. |
| 5,334,144 A | 8/1994 | Alchas et al. |
| 5,342,308 A | 8/1994 | Boschetti |
| 5,350,367 A | 9/1994 | Stiehl et al. |
| 5,354,286 A | 10/1994 | Mesa et al. |
| 5,358,489 A | 10/1994 | Wyrick |
| RE34,845 E | 1/1995 | Vetter et al. |
| 5,391,151 A | 2/1995 | Wilmot |
| 5,405,362 A | 4/1995 | Kramer et al. |
| 5,415,648 A | 5/1995 | Malay et al. |
| 5,425,715 A | 6/1995 | Dalling et al. |
| 5,451,210 A | 9/1995 | Krammer et al. |
| 5,478,316 A | 12/1995 | Bitdinger et al. |

(56) References Cited

U.S. PATENT DOCUMENTS

| | | | |
|---|---|---|---|
| 5,505,694 A | 4/1996 | Hubbard et al. | |
| 5,514,097 A | 5/1996 | Knauer | |
| 5,514,107 A | 5/1996 | Haber et al. | |
| 5,540,664 A | 7/1996 | Wyrick | |
| 5,542,760 A | 8/1996 | Chanoch et al. | |
| 5,544,234 A | 8/1996 | Terajima et al. | |
| 5,549,561 A | 8/1996 | Hjertman | |
| 5,554,134 A | 9/1996 | Bonnichsen | |
| 5,562,625 A | 10/1996 | Stefancin, Jr. | |
| 5,567,160 A | 10/1996 | Massino | |
| 5,569,190 A | 10/1996 | D'Antonio | |
| 5,569,192 A | 10/1996 | van der Wal | |
| 5,569,236 A | 10/1996 | Kriesel | |
| 5,573,042 A | 11/1996 | De Haen | |
| 5,593,388 A | 1/1997 | Phillips | |
| 5,599,302 A | 2/1997 | Lilley et al. | |
| 5,599,309 A | 2/1997 | Marshall et al. | |
| 5,605,542 A | 2/1997 | Tanaka et al. | |
| 5,637,094 A | 6/1997 | Stewart, Jr. et al. | |
| 5,649,912 A | 7/1997 | Peterson | |
| 5,658,259 A | 8/1997 | Pearson et al. | |
| 5,665,071 A | 9/1997 | Wyrick | |
| 5,688,251 A | 11/1997 | Chanoch | |
| 5,695,472 A | 12/1997 | Wyrick | |
| 5,704,911 A | 1/1998 | Parsons | |
| 5,725,508 A | 3/1998 | Chanoch et al. | |
| 5,730,723 A | 3/1998 | Castellano et al. | |
| 5,743,889 A | 4/1998 | Sams | |
| 5,769,138 A | 6/1998 | Sadowski et al. | |
| 5,785,691 A | 7/1998 | Vetter et al. | |
| 5,788,670 A | 8/1998 | Reinhard et al. | |
| 5,801,057 A | 9/1998 | Smart et al. | |
| 5,807,309 A | 9/1998 | Lundquist et al. | |
| 5,820,602 A | 10/1998 | Kovelman et al. | |
| 5,820,622 A | 10/1998 | Gross et al. | |
| 5,827,232 A | 10/1998 | Chanoch et al. | |
| 5,836,911 A | 11/1998 | Marzynski et al. | |
| 5,839,715 A * | 11/1998 | Leinsing | A61J 1/2096 251/149.1 |
| 5,843,036 A | 12/1998 | Olive et al. | |
| 5,846,233 A | 12/1998 | Lilley et al. | |
| 5,851,197 A | 12/1998 | Marano et al. | |
| 5,851,198 A | 12/1998 | Castellano et al. | |
| 5,860,456 A | 1/1999 | Bydlon et al. | |
| 5,865,795 A | 2/1999 | Schiff et al. | |
| 5,865,799 A | 2/1999 | Tanaka et al. | |
| 5,868,711 A | 2/1999 | Kramer et al. | |
| 5,873,857 A | 2/1999 | Kriesel | |
| 5,875,976 A | 3/1999 | Nelson et al. | |
| 5,879,327 A | 3/1999 | DeFarges et al. | |
| 5,891,085 A | 4/1999 | Lilley et al. | |
| 5,891,086 A | 4/1999 | Weston | |
| 5,893,397 A | 4/1999 | Peterson et al. | |
| 5,893,842 A | 4/1999 | Imbert | |
| 5,899,888 A * | 5/1999 | Jepson | A61J 1/2089 604/201 |
| 5,919,159 A | 7/1999 | Lilley et al. | |
| 5,921,966 A | 7/1999 | Bendek et al. | |
| 5,925,017 A | 7/1999 | Kriesel et al. | |
| 5,928,205 A | 7/1999 | Marshall | |
| 5,935,949 A | 8/1999 | White | |
| 5,951,528 A | 9/1999 | Parkin | |
| 5,957,897 A | 9/1999 | Jeffrey | |
| 5,960,797 A | 10/1999 | Kramer et al. | |
| 5,989,227 A | 11/1999 | Vetter et al. | |
| 6,004,297 A | 12/1999 | Steenfeldt-Jensen et al. | |
| 6,045,534 A | 4/2000 | Jacobson et al. | |
| 6,056,716 A | 5/2000 | D'Antonio et al. | |
| 6,077,247 A | 6/2000 | Marshall et al. | |
| 6,083,201 A | 7/2000 | Skinkle | |
| 6,090,070 A | 7/2000 | Hager et al. | |
| 6,099,504 A | 8/2000 | Gross et al. | |
| 6,123,684 A | 9/2000 | Deboer et al. | |
| 6,132,395 A | 10/2000 | Landau et al. | |
| 6,159,181 A | 12/2000 | Crossman et al. | |
| 6,171,276 B1 | 1/2001 | Lippe et al. | |
| 6,186,997 B1 * | 2/2001 | Gabbard | A61J 1/10 206/828 |
| 6,203,529 B1 | 3/2001 | Gabriel et al. | |
| 6,210,369 B1 | 4/2001 | Wilmot et al. | |
| 6,221,046 B1 | 4/2001 | Burroughs et al. | |
| 6,221,053 B1 | 4/2001 | Walters et al. | |
| 6,223,408 B1 | 5/2001 | Vetter et al. | |
| 6,231,540 B1 | 5/2001 | Smedegaard | |
| 6,241,709 B1 | 6/2001 | Bechtold et al. | |
| 6,245,347 B1 | 6/2001 | Zhang et al. | |
| 6,258,078 B1 | 7/2001 | Thilly | |
| 6,264,629 B1 | 7/2001 | Landau | |
| 6,270,479 B1 | 8/2001 | Bergens et al. | |
| 6,309,371 B1 | 10/2001 | Deboer et al. | |
| 6,319,224 B1 | 11/2001 | Stout et al. | |
| 6,371,939 B2 | 4/2002 | Bergens et al. | |
| 6,383,168 B1 | 5/2002 | Landau et al. | |
| 6,391,003 B1 | 5/2002 | Lesch, Jr. | |
| 6,406,456 B1 | 6/2002 | Slate et al. | |
| 6,428,528 B2 | 8/2002 | Sadowski et al. | |
| 6,471,669 B2 | 10/2002 | Landau | |
| 6,494,865 B1 | 12/2002 | Alchas | |
| 6,517,517 B1 | 2/2003 | Farrugia et al. | |
| 6,530,904 B1 | 3/2003 | Edwards et al. | |
| 6,544,234 B1 | 4/2003 | Gabriel | |
| 6,562,006 B1 | 5/2003 | Hjertman et al. | |
| 6,565,553 B2 | 5/2003 | Sadowski et al. | |
| 6,568,259 B2 | 5/2003 | Saheki et al. | |
| 6,569,123 B2 | 5/2003 | Alchas et al. | |
| 6,569,143 B2 | 5/2003 | Alchas et al. | |
| 6,584,910 B1 | 7/2003 | Plass | |
| 6,589,210 B1 | 7/2003 | Rolfe | |
| 6,607,508 B2 | 8/2003 | Knauer | |
| 6,620,137 B2 | 9/2003 | Kirchhofer et al. | |
| 6,641,561 B1 | 11/2003 | Hill et al. | |
| 6,645,170 B2 | 11/2003 | Landau | |
| 6,656,150 B2 | 12/2003 | Hill et al. | |
| 6,673,035 B1 | 1/2004 | Rice et al. | |
| 6,682,504 B2 | 1/2004 | Nelson et al. | |
| 6,689,092 B2 | 2/2004 | Zierenberg et al. | |
| 6,706,000 B2 | 3/2004 | Perez et al. | |
| 6,746,429 B2 | 6/2004 | Sadowski et al. | |
| 6,767,336 B1 | 7/2004 | Kaplan | |
| 6,805,686 B1 | 10/2004 | Fathallah et al. | |
| 6,830,560 B1 | 12/2004 | Gross et al. | |
| 6,899,698 B2 | 5/2005 | Sams | |
| 6,932,793 B1 | 8/2005 | Marshall et al. | |
| 6,932,794 B2 | 8/2005 | Giambattista et al. | |
| 6,936,032 B1 | 8/2005 | Bush, Jr. et al. | |
| 6,969,370 B2 | 11/2005 | Langley et al. | |
| 6,969,372 B1 | 11/2005 | Halseth | |
| 6,979,316 B1 | 12/2005 | Rubin et al. | |
| 6,986,758 B2 | 1/2006 | Schiffmann | |
| 6,997,901 B2 | 2/2006 | Popovsky | |
| 7,018,364 B2 | 3/2006 | Giambattista et al. | |
| 7,066,907 B2 | 6/2006 | Crossman et al. | |
| 7,112,187 B2 | 9/2006 | Karlsson | |
| 7,118,552 B2 | 10/2006 | Shaw et al. | |
| 7,118,553 B2 | 10/2006 | Scherer | |
| 7,169,132 B2 | 1/2007 | Bendek et al. | |
| 7,195,616 B2 | 3/2007 | Diller et al. | |
| 7,218,962 B2 | 5/2007 | Freyman | |
| 7,220,247 B2 | 5/2007 | Shaw et al. | |
| 7,247,149 B2 | 7/2007 | Beyerlein | |
| 7,291,132 B2 | 11/2007 | DeRuntz et al. | |
| 7,292,885 B2 | 11/2007 | Scott et al. | |
| 7,297,136 B2 | 11/2007 | Wyrick | |
| 7,341,575 B2 | 3/2008 | Rice et al. | |
| 7,361,160 B2 | 4/2008 | Hommann et al. | |
| 7,390,314 B2 | 6/2008 | Stutz, Jr. et al. | |
| 7,390,319 B2 | 6/2008 | Friedman | |
| 7,407,492 B2 | 8/2008 | Gurtner | |
| 7,416,540 B2 | 8/2008 | Edwards et al. | |
| 7,442,185 B2 | 10/2008 | Amark et al. | |
| 7,449,012 B2 | 11/2008 | Young et al. | |
| 7,488,308 B2 | 2/2009 | Lesch, Jr. | |
| 7,488,313 B2 | 2/2009 | Segal et al. | |
| 7,488,314 B2 | 2/2009 | Segal et al. | |

(56) References Cited

U.S. PATENT DOCUMENTS

| | | |
|---|---|---|
| 7,500,964 B2 | 3/2009 | Shaw et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,635,350 B2 | 12/2009 | Scherer |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Arby et al. |
| 2001/0039394 A1 | 11/2001 | Weston |
| 2001/0049496 A1 | 12/2001 | Kirchhofer et al. |
| 2002/0007149 A1 | 1/2002 | Nelson et al. |
| 2002/0045866 A1 | 4/2002 | Sadowski et al. |
| 2002/0173752 A1 | 11/2002 | Polzin |
| 2002/0183690 A1 | 12/2002 | Amisolle |
| 2002/0188251 A1 | 12/2002 | Staylor et al. |
| 2003/0040697 A1 | 2/2003 | Pass et al. |
| 2003/0083621 A1 | 5/2003 | Shaw et al. |
| 2003/0105430 A1 | 6/2003 | Lavi et al. |
| 2003/0130619 A1 | 7/2003 | Safabash et al. |
| 2003/0158523 A1 | 8/2003 | Hjertman et al. |
| 2003/0171717 A1 | 9/2003 | Farrugia et al. |
| 2003/0229330 A1 | 12/2003 | Hickle |
| 2003/0236502 A1 | 12/2003 | De La Serna et al. |
| 2004/0039336 A1 | 2/2004 | Amark et al. |
| 2004/0039337 A1 | 2/2004 | Letzing |
| 2004/0097783 A1 | 5/2004 | Peters et al. |
| 2004/0097883 A1 | 5/2004 | Roe |
| 2004/0143213 A1 | 7/2004 | Hunter et al. |
| 2004/0220524 A1 | 11/2004 | Sadowski et al. |
| 2004/0267207 A1 | 12/2004 | Veasey et al. |
| 2004/0267355 A1 | 12/2004 | Scott et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0080377 A1 | 4/2005 | Sadowski et al. |
| 2005/0101919 A1 | 5/2005 | Brunnberg |
| 2005/0165360 A1 | 7/2005 | Stamp |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0025747 A1 | 2/2006 | Sullivan et al. |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0060904 A1* | 3/2007 | Vedrine ............ A61J 1/2096 604/411 |
| 2007/0088288 A1 | 4/2007 | Barron et al. |
| 2007/0093775 A1 | 4/2007 | Daly |

(56) References Cited

U.S. PATENT DOCUMENTS

| | | |
|---|---|---|
| 2007/0100288 A1 | 5/2007 | Bozeman et al. |
| 2007/0123818 A1 | 5/2007 | Griffiths et al. |
| 2007/0123829 A1 | 5/2007 | Atterbury et al. |
| 2007/0129686 A1 | 6/2007 | Daily et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0154200 A1 | 6/2008 | Lesch |
| 2008/0185069 A1 | 8/2008 | Clark |
| 2008/0262427 A1 | 10/2008 | Hommann |
| 2008/0262436 A1 | 10/2008 | Olson |
| 2008/0262445 A1 | 10/2008 | Hsu et al. |
| 2009/0036866 A1* | 2/2009 | Moy ............ A61J 1/1475 604/416 |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0216212 A1* | 8/2009 | Fangrow, Jr. ....... A61J 1/2096 604/406 |
| 2009/0254027 A1 | 10/2009 | Moller |
| 2009/0254035 A1 | 10/2009 | Kohlbrenner et al. |
| 2009/0292240 A1 | 11/2009 | Kramer et al. |
| 2009/0299278 A1 | 12/2009 | Lesch, Jr. et al. |
| 2009/0304812 A1 | 12/2009 | Staniforth et al. |
| 2009/0312705 A1 | 12/2009 | Grunhut |
| 2009/0318361 A1 | 12/2009 | Noera et al. |
| 2010/0016326 A1 | 1/2010 | Will |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0114058 A1 | 5/2010 | Weitzel et al. |
| 2010/0121272 A1 | 5/2010 | Marshall et al. |
| 2010/0137798 A1 | 6/2010 | Streit et al. |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0191217 A1 | 7/2010 | Hommann et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0262083 A1 | 10/2010 | Grunhut et al. |
| 2010/0268170 A1 | 10/2010 | Carrel et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0292653 A1 | 11/2010 | Maritan |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janet et al. |
| 2011/0034879 A1 | 2/2011 | Crow |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0098656 A1 | 4/2011 | Burnell et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0137247 A1 | 6/2011 | Mesa et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Cleathero |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0172885 A1 | 7/2012 | Drapeau et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Born et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggermann et al. |
| 2012/0271243 A1 | 10/2012 | Plumptre et al. |
| 2012/0277724 A1 | 11/2012 | Larsen et al. |

(56) References Cited

U.S. PATENT DOCUMENTS

| | | |
|---|---|---|
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommerau |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | P1712805 | 10/2012 |
| BR | P10713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |

(56) References Cited

FOREIGN PATENT DOCUMENTS

| | | |
|---|---|---|
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 101563124 | 11/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023982 | 10/2012 |
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 0072057 | 2/1983 |
| EP | 0103664 | 3/1984 |
| EP | 1752174 | 3/1986 |
| EP | 245895 | 11/1987 |
| EP | 255044 | 2/1988 |
| EP | 361668 | 4/1990 |
| EP | 0518416 | 12/1992 |
| EP | 525525 | 2/1993 |
| EP | 1067823 | 1/2001 |
| EP | 1161961 | 12/2001 |
| EP | 1307012 | 5/2003 |
| EP | 1518575 | 3/2005 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| FR | 2506161 | 11/1982 |
| FR | 2635009 | 2/1990 |
| GB | 6677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | HO9290012 | 11/1997 |
| JP | 10-507935 | 8/1998 |
| JP | 11-347121 | 12/1999 |
| JP | 2000-245839 | 9/2000 |
| JP | 2001-523485 | 11/2001 |
| JP | 2005516696 | 6/2005 |
| JP | 5016490 | 5/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 2010538744 | 12/2010 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519511 | 8/2012 |
| JP | 2012519514 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |

(56) References Cited

FOREIGN PATENT DOCUMENTS

| | | |
|---|---|---|
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 201258630 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |
| JP | 2012528629 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | WO 92/19296 | 11/1992 |
| WO | WO 94/09839 | 5/1994 |
| WO | WO 94/11041 | 5/1994 |
| WO | WO 95/29720 | 11/1995 |
| WO | WO 95/29730 | 11/1995 |
| WO | WO 96/21482 | 7/1996 |
| WO | WO 97/14455 | 4/1997 |
| WO | WO 97/21457 | 6/1997 |
| WO | WO 1997/41907 | 11/1997 |
| WO | WO 97/48430 | 12/1997 |
| WO | WO 1998/031369 | 7/1998 |
| WO | WO 1998/032451 | 7/1998 |
| WO | WO 9831369 | 7/1998 |
| WO | WO 9832451 | 7/1998 |
| WO | WO 99/03521 | 1/1999 |
| WO | WO 99/10030 | 3/1999 |
| WO | WO 99/22790 | 5/1999 |
| WO | WO 9922789 | 5/1999 |
| WO | WO 1999/062525 | 12/1999 |
| WO | WO 9962525 | 12/1999 |
| WO | WO 0006228 | 2/2000 |
| WO | WO 00/24441 | 5/2000 |
| WO | WO 00/29050 | 5/2000 |
| WO | WO 01/93926 | 12/2001 |
| WO | WO 02/083216 | 10/2002 |
| WO | WO 2002/089805 | 11/2002 |
| WO | WO 2089805 | 11/2002 |
| WO | WO 3047663 | 6/2003 |
| WO | 03066152 | 8/2003 |
| WO | WO 2003/070296 | 8/2003 |
| WO | WO 3068290 | 8/2003 |
| WO | WO 03070296 | 8/2003 |
| WO | WO 2003/097133 | 11/2003 |
| WO | WO 3097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/005929 | 1/2005 |
| WO | WO 20051/002653 | 1/2005 |
| WO | WO 2005/009515 | 2/2005 |
| WO | 2005032623 | 4/2005 |
| WO | WO 2005/053778 | 6/2005 |
| WO | WO 2006/079064 | 7/2006 |
| WO | WO 2006/086899 | 8/2006 |
| WO | WO 2006/125328 | 11/2006 |
| WO | WO 2006/130098 | 12/2006 |
| WO | WO 2007/047200 | 4/2007 |
| WO | WO 2007/063342 | 6/2007 |
| WO | WO 2007/100899 | 9/2007 |
| WO | WO 2006/079064 | 11/2007 |
| WO | WO 2007/131013 | 11/2007 |
| WO | WO 2007/131025 | 11/2007 |
| WO | WO 20071129106 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/089886 | 7/2008 |
| WO | WO 2008/100576 | 8/2008 |
| WO | WO 2008/107378 | 9/2008 |
| WO | WO 2008/112472 | 9/2008 |
| WO | WO 2007/104636 | 12/2008 |
| WO | 2009038860 | 3/2009 |
| WO | WO 2009049885 | 4/2009 |
| WO | WO 2008/071804 | 9/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |

(56) References Cited

FOREIGN PATENT DOCUMENTS

| | | |
|---|---|---|
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |
| WO | WO 2011/048223 | 4/2011 |
| WO | WO 2011/048422 | 4/2011 |
| WO | WO 2011/050359 | 4/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/060087 | 5/2011 |
| WO | WO 2011/067187 | 6/2011 |
| WO | WO 2011/067268 | 6/2011 |
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | WO 2011/107806 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/117404 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2011/042537 | 8/2012 |
| WO | WO 2011/042540 | 8/2012 |
| WO | WO 2011/043714 | 8/2012 |
| WO | WO 2011/051366 | 9/2012 |
| WO | WO 2012/122643 | 9/2012 |

OTHER PUBLICATIONS

Notification of Reasons for Refusal dated Sep. 20, 2016 for Japanese Patent Application No. 2014-520360.
International Patent Application No. PCT/US14/23883, International Search Report, dated Jul. 10, 2014, 3 pages.
International Patent Application No. PCT/US14/23485, International Search Report, dated Jul. 7, 2014, 2 pages.
International Patent Application No. PCT/US14/24530, International Search Report, dated Jul. 15, 2014, 2 pages.
International Patent Application No. PCT/US14/24543, International Search Report, dated Jul. 28, 2014, 2 pages.
"Skin", American Medical Association (AMA) Current Procedural Terminology, 1998, http://www.ama-assn.org/ama/pub/category/print/7176.html, 1 page.
Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306.
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1), pp. 73-81.
Chen et al., "Blood Lipid Profiles and Peripheral Blood Mononuclear Cell Cholesterol Metabolism Gene Expression in Patients with and Without Methotrexate" BMC Medicine, 2011, 9(4), 9 pages.
Chiasson et al., "Continuous Subcutaneous Insulin Infusion (Mill-Hill Infuser) Versus Multiple Injections (Medi-Jector) in the Treatment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with communication dated Apr. 25, 2005 regarding Proceeding Further with the European Patent Application Pursuant to Article 96(1), and Rule 51(1) EPC, 3 pages.
European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31(6), pp. 361-366.
Hoekstra et al., Bioavailability of Higher Dose Methotrexate Comparing Oral and Subcutaneous Administration in Patients with Rheumatoid Arthritis, The Journal of Rheumatology, 2004, 31(4), pp. 645-648.

(56) References Cited

OTHER PUBLICATIONS

International Patent Application No. PCT/US2012/46742, International Search Report and Written Opinion dated Nov. 16, 2012, 11 pages.
International Patent Application No. PCT/US2009/052835, International Search Report dated Mar. 15, 2010, 5 pages.
International Patent Application No. PCT/US2013/029085, International Search Report dated May 13, 2013, 2 pages.
International Patent Application No. PCT/US2010/028011, International Search Report, dated Jun. 29, 2010, 5 pages.
International Patent Application No. PCT/US2009/036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes care, Nov.-Dec. 1986, 9(6), 637-640.
"The Historical Development of Jet Injection and Envisioned Uses in Mass Immunization and Mass Therapy Based Upon Two Decades' Experience", Military Medicine, Jun. 1963, 128, pp. 516-524.
Pehling et al, "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US20131029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.
Tukova et al., "Methotrexate Bioavailability after Oral and Subcutaneous Administration in Children with Juvenile Idiopathic Arthritis", Clinical and Experimental Rheumatology, 2009, 27, 1047-1053.
Wright et al., "Stability of Methotrexate Injection in Prefilled Plastic Disposable Syringes", International Journal of Pharmaceutics, Aug. 1988, 45(3), 237-244.
Lunenfeld, "Stable Testosterone Levels Achieved with Subcutaneous Testosterone Injections", The aging Male, Mar. 2006, 9(1), 70 pages.
International Patent Application No. PCT/US2012/046639, International Search Report and Written Opinion of the International Searching Authority, dated Apr. 22, 2013. 8 pages.
Summary of Notification of Provisional Rejection dated Sep. 4, 2018 for Korean Patent Application No. 10-2014-7003621.

* cited by examiner

LIQUID-TRANSFER ADAPTER BEVELED SPIKE

CROSS REFERENCE TO RELATED APPLICATIONS

This application is a continuation of U.S. patent application Ser. No. 13/184,211, entitled "Liquid-Transfer Adapter Beveled Spike," filed on Jul. 15, 2011, the entire content of which is incorporated herein by reference.

TECHNICAL FIELD

The present application related generally to liquid-transfer adapters and, more specifically, to liquid-transfer adapters that provide liquid communication between vials and injectors.

BACKGROUND

In the medical field, it is common practice for medication to be provided in a vial. The medication is transferred from the vial to an injector (e.g., a syringe, auto-injector, jet injector, and so forth) for subsequent injection into a patient. In some cases, the medication is provided in a liquid solution in the sealed vial, while in other cases it is provided in a solid form (e.g., powder). Generally, when provided in solid form, a solvent (e.g., water) is inserted into the vial to dissolve the medication. The liquid medication is extracted out of the vial into an injector for injection into a patient.

A typical vial is sealed with a stopper that has sidewalls extending down the inside walls of a neck portion of the vial. Conventionally, a hollow spike has been implemented to provide fluid communication with the contents of the vial. In particular, the hollow spike punctures the stopper to insert and/or extract liquid from the vial. Occasionally, however, when attempting to puncture the stopper, the spike may inadvertently enter into a sidewall of the stopper, preventing or limiting liquid communication with the contents of the vials, depending on the orientation of the opening to draw the fluid from the vial into the spike.

Additionally, as conventional spikes are pushed through rubber stoppers, the rubber stoppers are often stretched, torn, or cut by the spike. In some cases portions of the stopper may enter into the hollow spike and may even core the stopper resulting in obstruction of liquid flow from the vial.

U.S. Pat. No. 5,254,106 discloses a needle that includes a slot that extends along the sidewalls of the needle. Similarly, U.S. Pat. Pub. No. 2006/0266431 discloses a needle with slots in the sidewall. U.S. Pat. No. 4,411,661 and U.S. Pat. Pub. No. 2007/0179506 disclose a spike with a slot that extends from a conical tip on its sidewalls. U.S. Pat. No. 7,150,735 discloses a spike with one or more openings in a beveled surface.

SUMMARY

A liquid-transfer adapter operatively interposable between an injector and a vial is provided. In some embodiments, the adapter has an injector engaging portion configured for fluidly coupling to an injector and a vial coupling. The vial coupling includes a spike that has a spike axis and a tip portion configured for piercing a septum of a vial. The tip portion includes a plurality of facets that meet each other at one or more edges and at least one of the one or more edges is sloped with respect to the spike axis. The spike defines a channel extending therethrough in fluid communication with the injector engaging portion. A channel opening is defined in at least one of the facets and disposed without interrupting the edges.

In some embodiments, the edges comprise junctions between the facets. The edges may also have cutting surfaces configured for cutting the septum as the spike is pushed therethrough. In one embodiment, the tip portion has at least three facets and the channel opening comprises a channel opening disposed in each of at least three of the facets. The channel the openings may be spaced circumferentially from the edges. Additionally, lateral edges of the channel openings may be disposed radially inward compared to the edges. Moreover, lateral edges of the channel openings are disposed radially inward relative to the edges at any axial position. The lateral edges of the channel openings may be spaced from the edges sufficiently to minimize intrusion of the septum into the channel openings when the spike is pierced through the septum. The channel openings may be substantially centered circumferentially on the facets. In some embodiments, a seal may be disposed at the injector engaging portion configured for mating with the injector for maintaining liquid within the channel and injector. Additionally, the injector engaging portion has dimensions suitable for coupling with a needle free injector. Moreover, a removable insert may be removably coupled within the injector engaging portion for selectively configuring the injector engaging portion for engaging variously sized injectors. The removable insert may have dimensions suitable for coupling with a syringe having a first width, and with the insert removed, the injector engaging portion is configured for coupling to a jet injector having a second width that is larger than the first width.

In some embodiments, a vial engaging member may be associated with the vial coupling portion and configured for engaging the adapter to the vial with the spike inserted therein. Moreover, the vial engaging member may include reflexed fingers arranged around the spike and extending theretowards for snapping to and retaining the adapter engaged to the vial. Further, the spike may include a shaft extending from the tip towards the injector engaging portion and an opening extends onto the shaft for maximizing fluid extraction from the vial with the vial in an inverted position.

In some embodiments, the edges meet at a point that is substantially axially centered. Additionally, the facets may be substantially flat bevels. In still other embodiments, a liquid-transfer adapter is provided having a spike for providing liquid communication to a sealed vial. The spike includes a shaft portion and a piercing point configured for piercing a septum of a vial. The tip includes at least three bevels joining together at a substantially centered tip, a channel extending through the spike, and a channel opening disposed within each bevel and onto the shaft portion. The channel openings are connected to the channel for transferring fluid to or from the vial.

BRIEF DESCRIPTION OF THE DRAWINGS

The drawings depict one or more implementations in accordance with the present concepts, by way of example only, not by way of limitation. In the drawings, like reference numerals refer to the same or similar elements.

DETAILED DESCRIPTION

Figure 1:
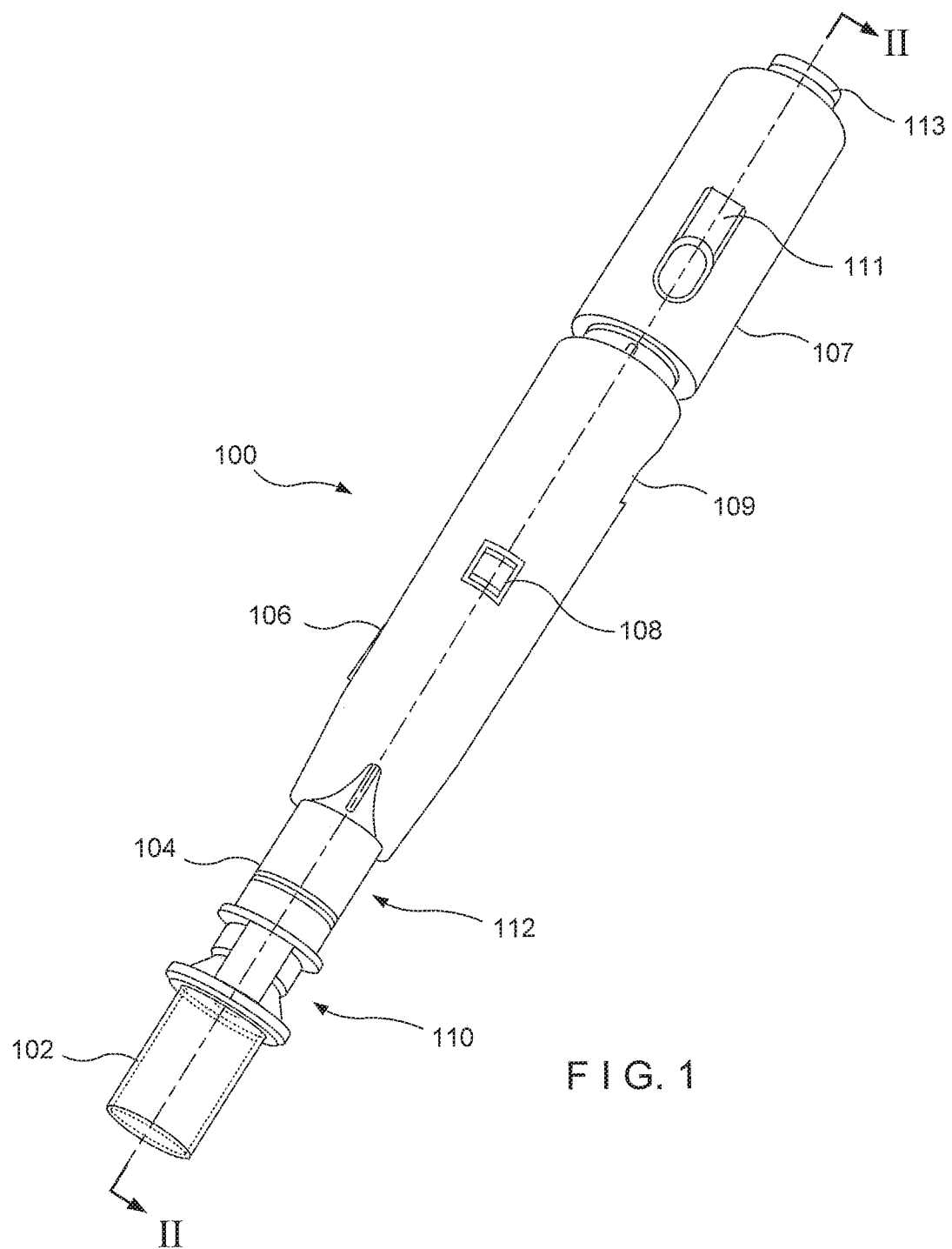
FIG. 1 shows a liquid-transfer system in accordance with an example embodiment.

Referring to FIG. 1, a liquid-transfer system 100 is illustrated in accordance with an example embodiment. Generally, the liquid-transfer system 100 includes a vial 102 holding liquid 103, a liquid-transfer adapter 104 and an injector 106. The liquid-transfer adapter 104 provides liquid communication between the vial 102 and the injector 106 to facilitate the transfer of liquid to and/or from the vial 102, and to and/or from the injector 106.

The injector 106 may have an indicator window 108 for indicating a volume of liquid 103 that it contains (e.g., the amount of liquid retrieved from the vial 102). The injector 106 may take one of several different forms, including a syringe, an auto injector, or a jet injector (needle free or needle-assisted). Information regarding injectors may be found in U.S. Pat. Nos. 5,875,976, 6,673,035, and/or 6,673,035, which are incorporated by reference herein in their entirety and for all purposes. It should be appreciated that the needle-free injectors described in these references can be adapted for needle-assisted injection, auto injection, and/or other types of injection.

The liquid-transfer adapter 104 can be operatively coupled in between the vial 102 and the injector 106. The liquid-transfer adapter 104 has a vial engaging end 110 that receives the vial 102 and couples the vial with the liquid-transfer adapter. Additionally, the liquid-transfer adapter 104 has an injector engaging end 112 to which the injector 106 can be attached.

Figure 2:
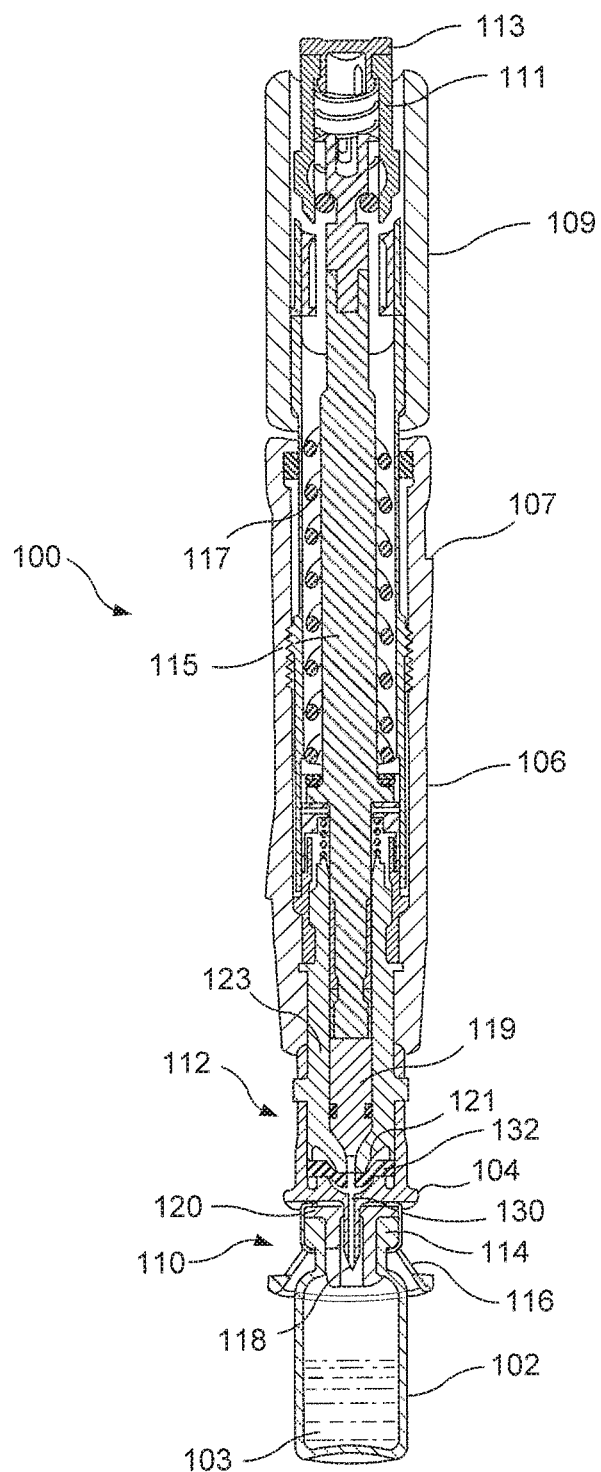
FIG. 2 is a cross-sectional view of the liquid-transfer system of FIG. 1 taken along line II-II.

FIG. 2 is a cross-sectional view of the liquid-transfer system of FIG. 1 taken along line II-II. As shown, the injector 106 includes a distal housing 107 and a proximal housing 109. The proximal housing 109 includes a trigger mechanism 111 and a button 113 for firing the injector 106. The distal housing 107 includes a ram 115 and an energy source 117 (e.g., a firing spring) associated therewith to provide energy for firing the injector 106. A firing stopper 119 may be attached to the proximal end of the ram 115 to force out fluid medicament through a jet nozzle 121 when the injector 106 is fired. Additionally, the firing stopper 119 moves proximally to draw liquid 103 from the vial 102 into a cartridge 123. A seal 132 interfaces the jet nozzle 121 and is generally located between the adapter and the distal end of the injector 106. The seal 132 may be provided maintain liquid within the channel and an injector coupled to the adapter 104.

Figure 3:
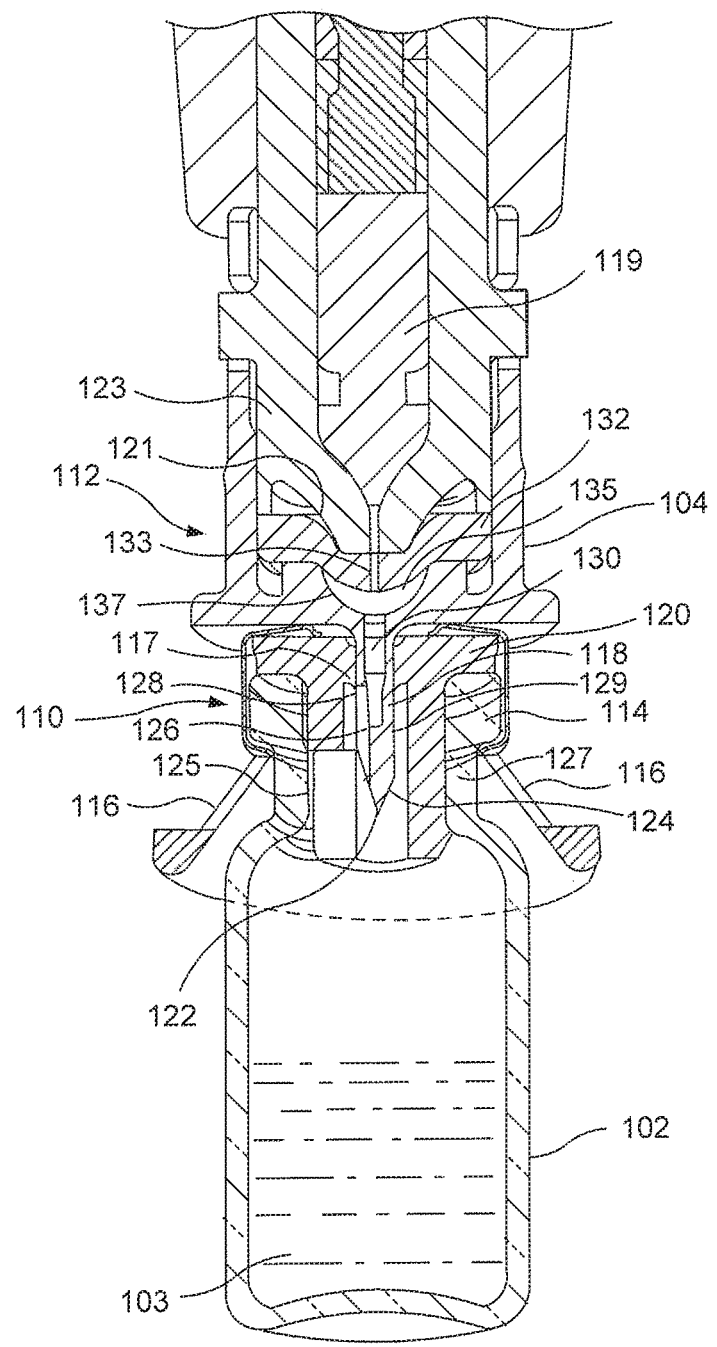
FIG. 3 is a cross-section view of a distal portion of the distal end of the adapter of FIG. 2 coupled to a vial.

FIG. 3 is an enlarged view of a portion of FIG. 2 showing the vial 102 and the adapter 104. The vial 102 preferably has a neck 125 and a lip 114 that protrudes radially beyond a recessed portion of the neck 127 which may be used to engage the vial 102 with the liquid-transfer adapter 104. Fingers 116 of the adapter can be provided to seat on and engage the lip 114 to hold the vial 102 in an engaged position with respect to the adapter 104. The fingers 116 may be arranged around the spike 118 and extending theretowards for snapping to and retaining the adapter 104 engaged to the vial 102.

The engagement of the vial 102 with the adapter 104 causes a spike 118 of the adapter 104 to puncture a septum (or stopper) 120 of the vial. The spike 118 may be a multifaceted spike having a tip 122 that is preferably axially centered with respect to the central axis of the spike 118. In such embodiments, the tip 122 can have a coaxial point, but in alternative embodiments, the tip and point can be provided off center. One or more facets 124 may include a channel opening 126. Some or all of the channel openings 126 extend on the facet 124 and onto the sidewall 128 of the shaft 129 of the spike 118. As the spike, 118 is pushed through the septum 120, the septum is deformed (as shown at 117) as the sidewall 128 of the shaft 129 pull on the septum. Preferably, the channel openings 126 extend down the sidewall 128 of the shaft 129 so that when the spike 118 is inserted through the septum 120 at least a portion of the channel openings are not exposed outside of the septum. The channel openings 126 are fluidly connected to an interior channel 130 that extends longitudinally through the spike 118 thereof. The openings 126 are generally spaced circumferentially from the edges. Further, the lateral edges of the openings 126 are radially positioned inwardly from the edges at any axial station. The channel 130 provides liquid communication between the vial engaging end 110 and the injector engaging end 112 of the adapter 104.

FIGS. 2 and 3 also show a seal 132, such as a rubber seal or elastomeric septum, which is positioned within the injector engaging end 112 over a terminal end of the channel 130 and configured to prevent fluid from leaking from the interface between the injector engaging end 112 and the injector 106 that is coupled therewith. The seal 132 includes an opening 133 to fluidly communicate the channel 130 to the injector 106. The seal 132 includes a domed region 135 that corresponds with a dome cutaway 137 in the adapter 102 and which helps to achieve a seal. Preferably, the jet nozzle 121 slightly deforms the seal 132 when the two are interfaced.

Figure 4:
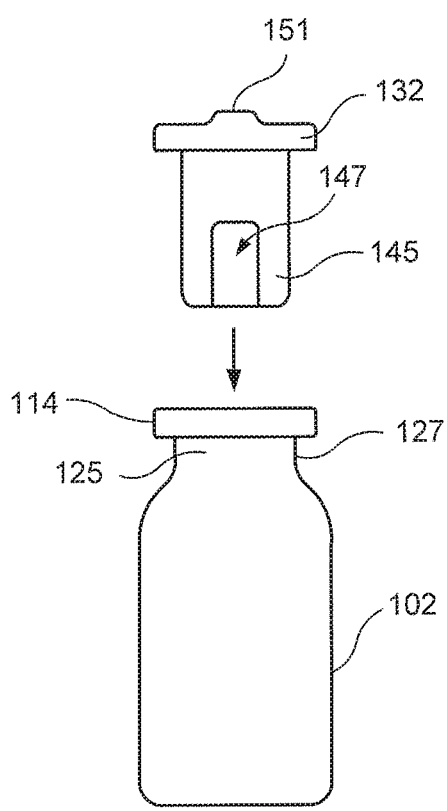
FIGS. 4-5 illustrate the vial before and after being sealed with a stopper 132, respectively.
Figure 5:
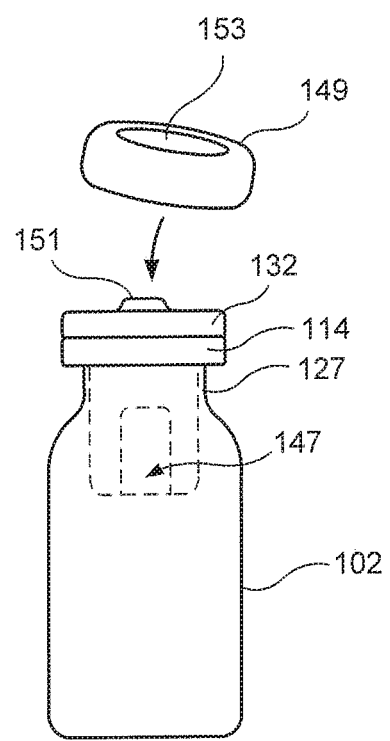

FIG. 4 illustrates the vial 102 before it is sealed with the stopper 132. The vial 102 has the recessed neck portion 127 and the lip 114. Medicament may be inserted into the vial 102 prior to placing the stopper within the neck 125 of the vial. The stopper 132 may include a generally cylindrical member 145 that is configured to extend into the neck 125 of the vial. Before sealing the vial 102, the stopper 132 may be partially inserted into the vial and medicament may be inserted through a gap 147 of the cylindrical member 145. The gap 147 may take the form of a shortened portion of the cylindrical member 145. The medicament may be placed in the vial in a liquid or a solid form. Additionally, in some embodiments, a liquid medicament inserted into the vial 102 may be heated or otherwise treated so as to be solid before fully inserting the stopper 132. Once the stopper 132 is fully inserted into the vial 102, a cap 149 (e.g., a metal cap) is positioned over the stopper and may subsequently be crimped about the lip 114 of the vial to secure the stopper and seal the vial. The cap 149 may have a removable tab 153 that may be removed for insertion of a spike, such as the spike 118 of the adapter 104. The stopper 132 may have a circular protrusion 151 on its top that may serve to provide a target for the spike. The removable tab 153 may be generally centered over this protrusion 151 in some embodiments so that when it is removed the protrusion is exposed. It should be appreciated that the stopper 132 and/or vial 102 may be provided in a variety of different sizes and/or dimensions.

Figure 6:
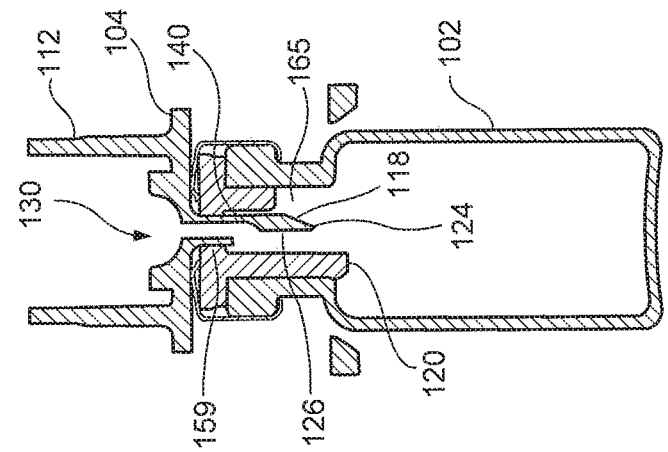
FIGS. 6-8 are cross-sectional views of various adapter configurations to connect to various sizes of vials for liquid-transfer.
Figure 7:
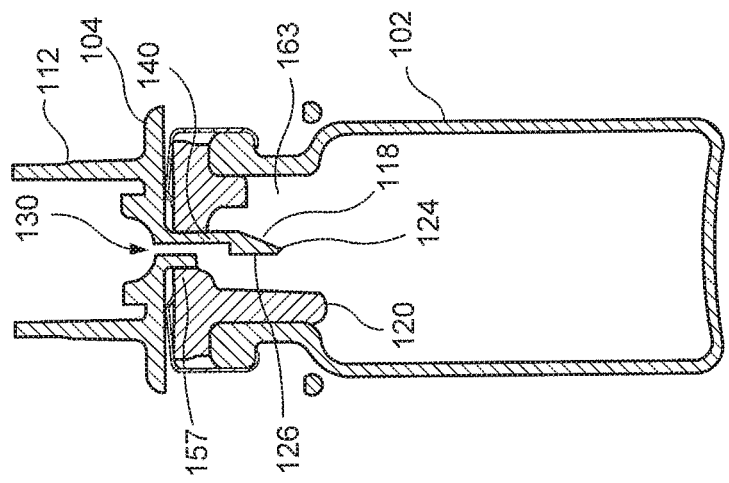
Figure 8:
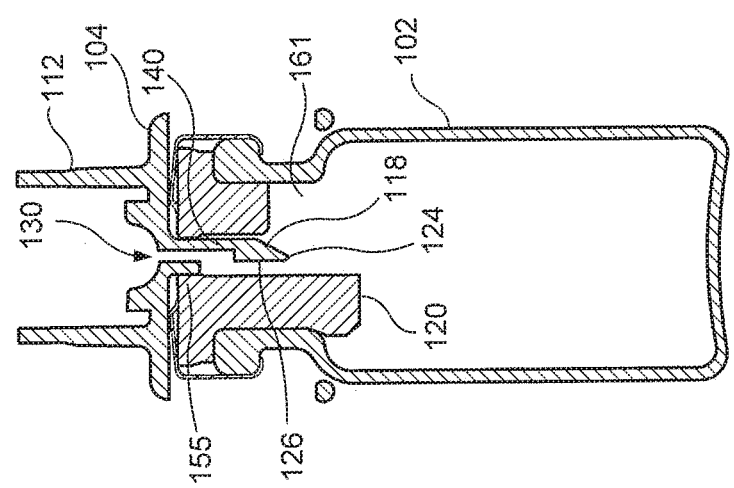

FIGS. 6-8 show the cross-sectional views of the adapter 104 with the vial 102 with the stoppers in each having different dimensions. Specifically, FIG. 6 illustrates a Ferring 20 mm stopper 155, FIG. 7 illustrates a Teva 20 mm stopper 157, and FIG. 8 illustrates a Ferring 13 mm stopper 159. Each of the stoppers 155, 157 and 159 has a gap 161, 163, and 165. The spike 118 can have the same dimensions in adapters sized for use with different vials, such as in each of the adapters in FIGS. 6-8. This can allow a common mold may be used for the spike 118 that is functional in a variety of adapters and with a variety of vial and stopper sizes. As such, molds for the other parts of the adapter 104 may vary but only a single mold need be designed and prepared for the spike 118 in this embodiment, thus providing manufacturing efficiency and savings.

As may be seen in FIGS. 6-8, channels 126 of the spike preferably extend onto the sidewall 128 from the facets 124 to a distance from the tip that is sufficient so that a portion of the channel 126 is submerged within the septum 120. It should be appreciated, that there is some deformation of the center portions 155, 157, 159 of the septums 120 when the spike is pushed through, as shown in FIG. 3 at 117. The deformation is not shown in FIG. 6-8. However, generally, the channel 126 of the spike 118 terminates at some point within the center portions 155, 157,159 of the septums 120 so that when the coupled vial, adapter, and injector are inverted with the vial on top, the amount of fluid that can be withdrawn from the vial is maximized compared to having the channel openings 126 terminate outside of the septum 120. In an alternative embodiment, however, some or all of the channel openings 126 can be shorter so as to remain spaced from the septum 120 when the spike is fully inserted therein.

It should be appreciated that the extent to which a portion of the aperture remains within the septum 120 and/or the extent to which the end 140 of the channel 126 extends beyond the septum may depend on several factors such as the thickness of the septum, the length of the channel and/or the extent to which the channels extend down the sidewall of the spike. It should be appreciated, however, that preferably the dimensions of the spike 118 are such that they function as intended for a variety of different dimensioned septums/stoppers and/or vials. As such, the tooling for the spike 118 can be reused. The adapter 104 dimensions may vary to accommodate the different sizes of vial necks, for instance. In other embodiments, the dimensions of the spike may vary and tooling may be created to accommodate various spike sizing/dimensions.

Figure 9:
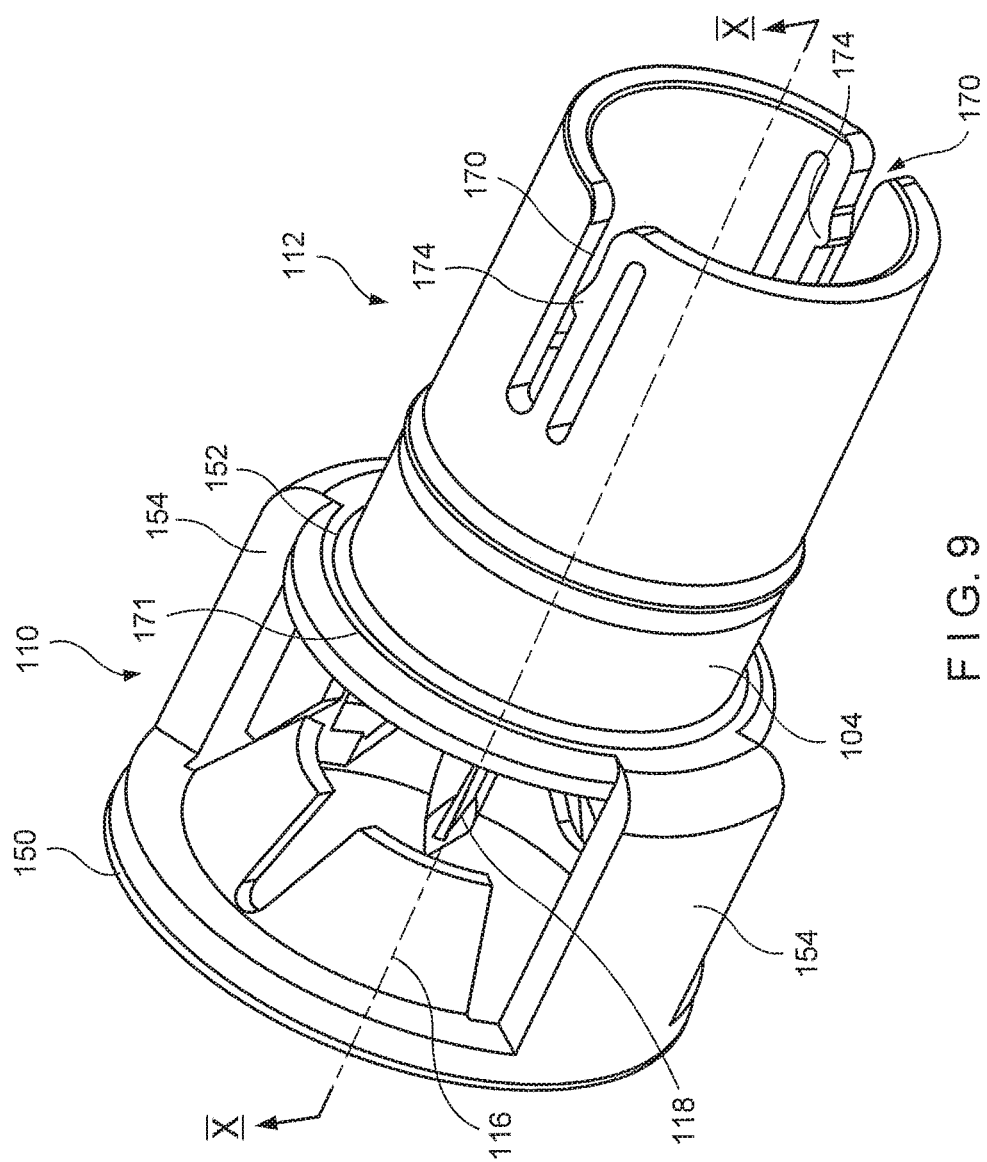
FIG. 9 is a perspective view of the liquid-transfer adapter of FIG. 1.

FIG. 9 is a perspective view of the liquid-transfer adapter 104 without a vial. The vial engaging end 110 includes a collar 150 that couples to a center body 152 of the adapter with support structures 154. The center body 152 preferably includes a wall 171 that divides the vial and injector engaging ends from each other, and the spike 118 preferably extends from the center body 152. The collar 150 is held by the support structures 152 at a distance from the center body 152 greater than the length of the spike 118. Fingers 116 are distributed about the collar 150 and extend inwardly from the collar 150 towards the spike 118. The fingers 116 may be reflexed so as to snap to the vial and retain the adapter engaged to the vial. Other embodiments may use different mechanisms to engage the adapter to the vial.

Engagement slots 170 on the injector engaging end 112 having engagement members 174 are also shown in FIG. 9. Generally, the engagement slots 170 may be configured to releasably receive and engage flanges of an injector or an adapter. Engagement members 174 may generally be resilient protrusions into the slots 170 configured to hold the flanges and the injector or adapter in a coupled position relative to the adapter 104.

Figure 10:
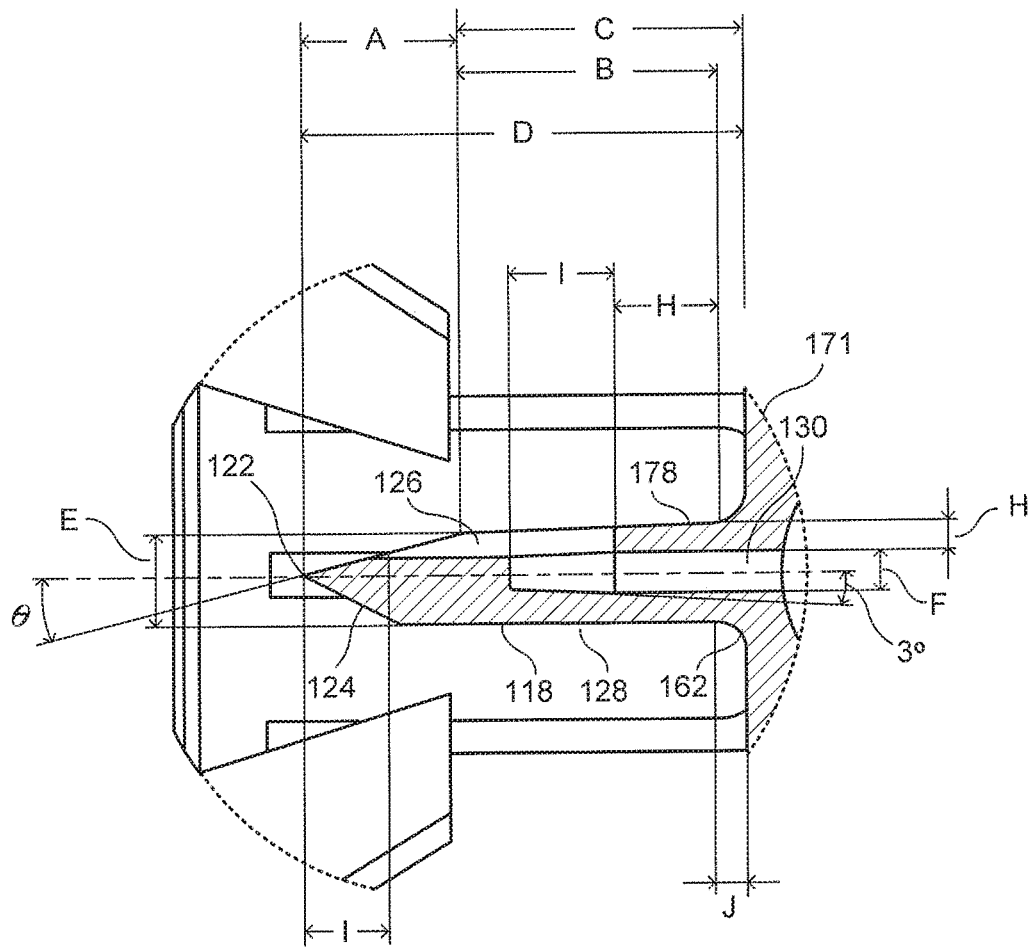
FIG. 10 is an enlarged cross-sectional view of the liquid-transfer adapter of FIG. 9 taken along line X-X.

FIG. 10 is an enlarged cross-sectional view of the liquid-transfer adapter 104 of FIG. 9 taken along line X-X. While particular dimensions of the adapter 104 may vary, some example dimensions are provided herein to give a sense of the scale for a preferred adapter. For example, the distance from an outer edge 160 of the collar 150 to the end of the fingers 116 may be, for example, up to around a half of an inch but preferably between about 0.1-0.4 inches, and in one embodiment about a quarter inch. A plurality of fingers 116 may be provided, such as four fingers 116 provided in pairs 180, and configured with a desired stiffness for coupling with the vial. A length of the injector engaging end 112 is typically between about half an inch to an inch or greater, and in one embodiment is approximately 0.8 inches. Additionally, the diameter of the injector engaging end may be up to or greater than about one inch and preferably between 0.4-0.7 inches, for example about half an inch, and in one embodiment about 0.6 inches.

The tip 122 of the spike is shown as axially centered with the spike 118, although in other embodiments the spike may not be axially centered (e.g., may be offset from the center). Generally, the beveled facets 124 may have and angle $\theta$ relative to the axis of the spike 118 that is suitable for injection through skin. For example, the angle $\theta$ may be up to about 45 degrees relative to the axis of the spike 118 and typically between about 10-20 degrees, or approximately 15 degrees in an embodiment. The beveled facets 124 may have a length A between 0.1-0.17 inches and in one embodiment 0.14 inches longitudinally along the spike 118. A length B along the shaft of the spike from the bevel to a curved portion of the base 162 may be between 0.21-0.26 inches and in one embodiment may be 0.24 inches. The curved portion of the base J may be between 0.01-0.03 inches and in one embodiment approximately 0.02 inches. A length C along the shaft of the spike 118 that includes the curved base 162 may be between 0.22-0.27 inches and may be 0.25 inches in one embodiment. As such, the ratios A/B and A/C may each be between approximately ⅓ to ¾.

The spike 118 may generally have a length D of up to or greater than about half of an inch or longer, and is preferably between about 0.3 and 0.5 inches, and in one embodiment is approximately 0.4 inches. The ratio of A/D may be between ⅕ to ⅔. The spike 118 may have a width E, typically, of about 0.05 to 0.2 inches, preferably between 0.07-0.1 inches, and in one embodiment about 0.08 inches. The width E of the shaft may be slightly larger at a base 162 of the shaft 178. The channel 130 extends through the center of the spike 118 and may have a diameter F that may be between about 0.03-0.06 inches, and in one embodiment is about 0.04 or 0.05 inches and tapers proximally downward. The downward taper may begin where an overlap occurs between the channel 130 and the opening 126. The channel 130 may have a length between 0.1-0.2 inches from the base 162 of the shaft 178 to where the overlap occurs. The overlap of the channel and channel overlap may have a length between 0.08-0.1 inches. The channel 130 may have a depth H between 0.02 and 0.03 inches, and in one embodiment may be approximately 0.025 inches. A ratio H/E may be between approximately ¼ and ⅓. A longitudinal distance I from the tip 122 to the channel opening may be between 0.06 and 0.08 inches, and in one embodiment may be 0.07 inches. A ratio A/I may be between approximately two and ¾.

Figure 11:
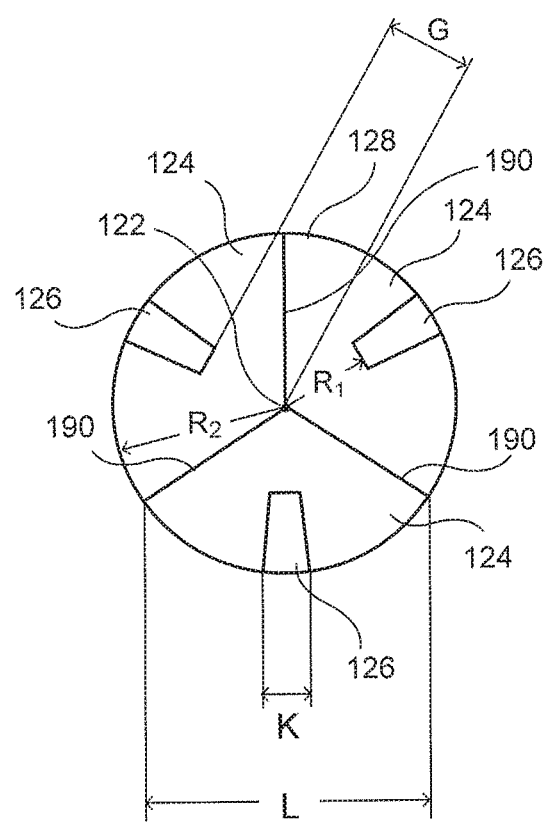
FIG. 11 is an axial view of the adapter of FIG. 9 from a vial coupling end.

FIG. 11 illustrates the spike tip 122 as having three facets or bevels that converge to a point 122. The facets 124 meet at edges 190 and channel openings 126 are located within the facets but do not interrupt the edges. The channel openings 126 may generally have a width J between 0.01-0.02 inches, and preferably approximately 0.015 inches, while the facets 124 may generally each have an arcuate length between edges of approximately 0.06 and 0.1 inches, and preferably about 0.08 inches. A ratio of J/K may be between ⅒ and ⅓.

The channel openings 126 are preferably generally centered within the facets 124 so that they do not extend to the junctions of the facets. Thus, the lateral edges of the openings 126 are disposed radially inward compared to the edges 190 and are spaced circumferentially from the edges. This is true at any axial station. As such a radius R1 measured radially from the axis to the openings 126 is less than a radius R2 from the axis to the edge 190. The openings 126 in this embodiment are about 120 degrees apart on center, seen in an axial direction, since they are preferably about equally spaced and centered on the facets 124. The facets 124 may be spaced about the tip of the spike 118 in any suitable manner. In some embodiments, the each facet is the same size as the others, while in other embodiments one or more facets may be differently sized from the others. In an example, one or more facet 124 may have a width less than a tenth of an inch where it meets the sidewall 128 of the shaft. In one embodiment, the channel openings 126 may be up to about 30 degrees wide, measured on a radial plane, about the center and preferably between 5-30 degrees wide (e.g., about 20 degrees wide in one embodiment). A distance G between the tip 122 and the channel openings 126 may be between 0.01-0.02 inches (e.g., 0.015 inches). The channel openings 126 are preferably tapered along the facets 124, but alternatively can have a substantially constant width.

It should be appreciated that the dimensions provided herein are merely exemplary and are not limiting. Indeed, in some embodiments the dimensions may be altered to accommodate certain functionality and/or to couple with injectors and/or vials having different dimensions.

Figure 12:
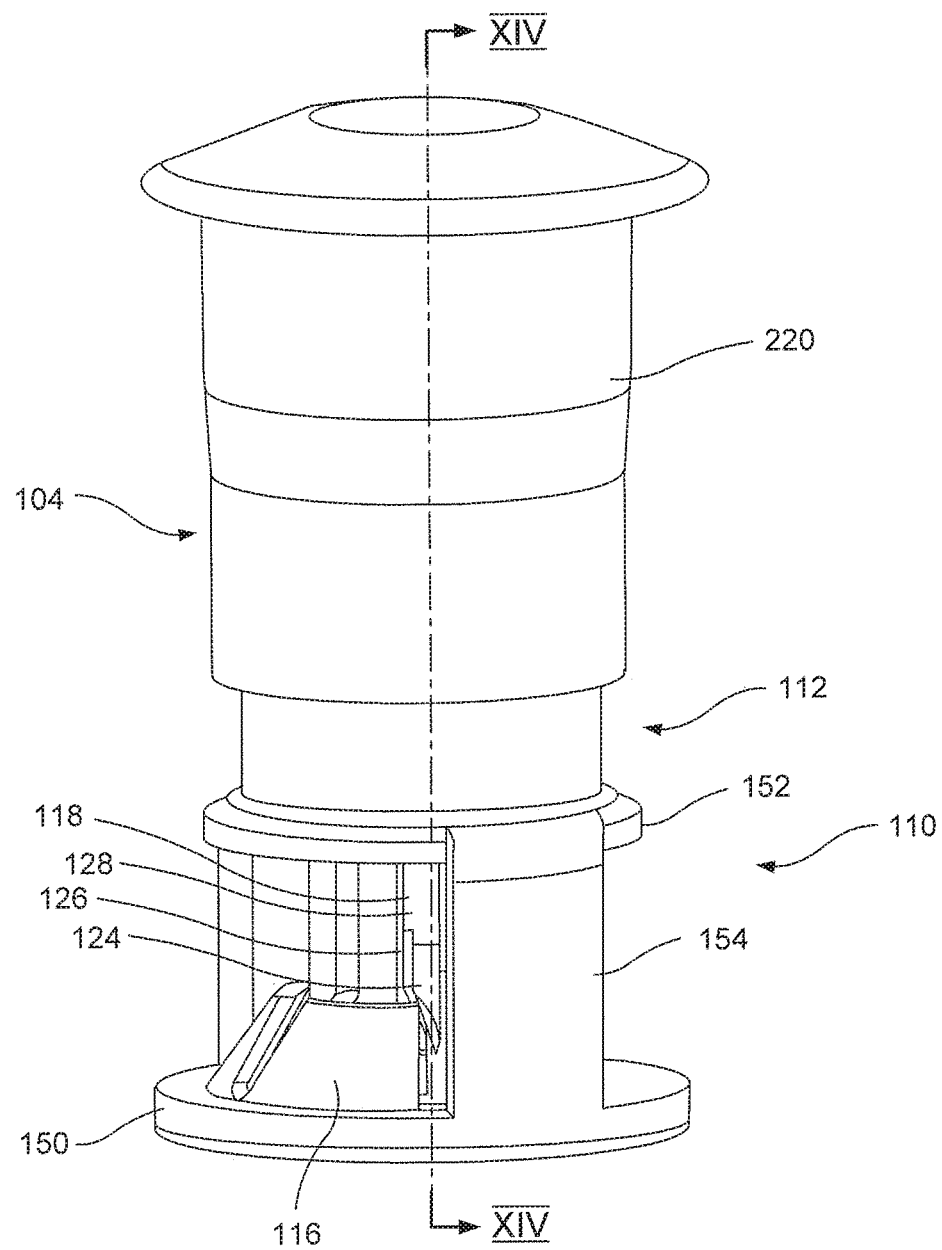
FIG. 12 illustrates a side view of the adapter of FIG. 1 having a cap prior to use of the adapter.
Figure 13:
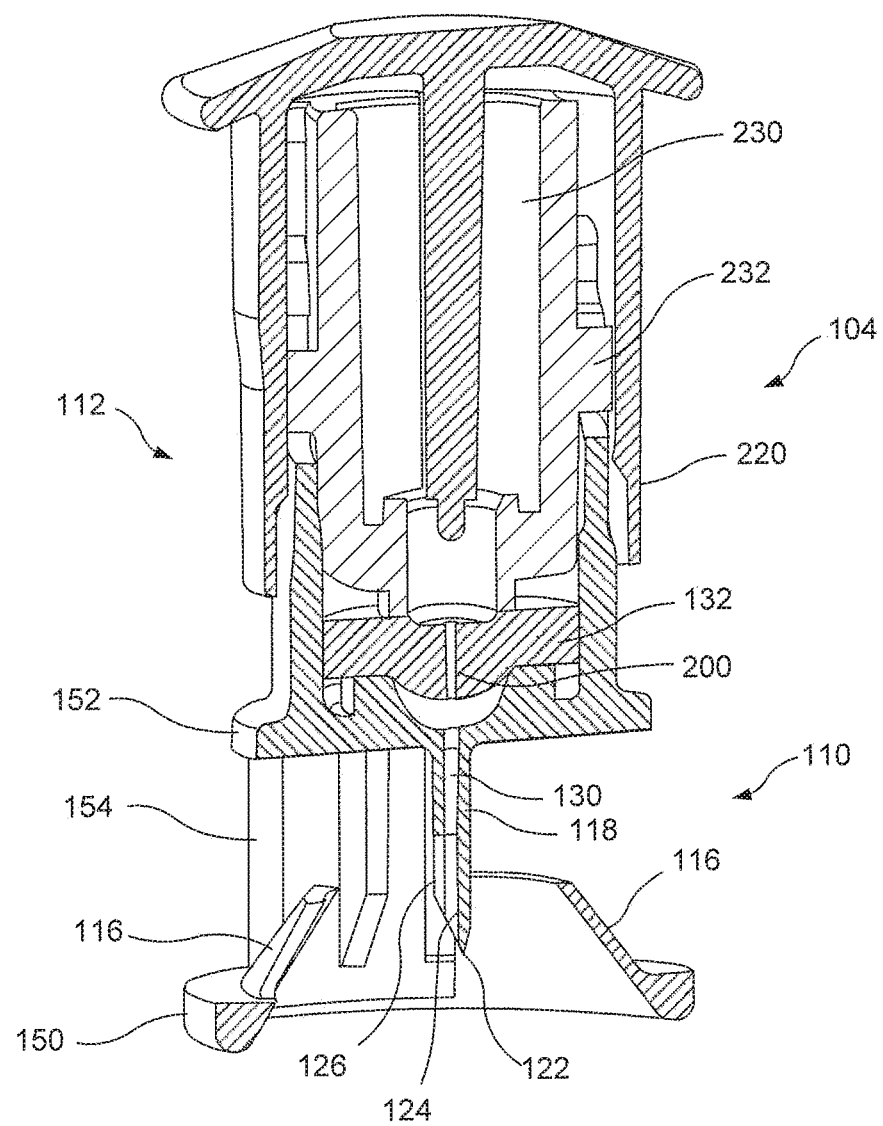
FIG. 13 is a cross-sectional view of the adapter shown in FIG. 12 taken along line XIV.

As illustrated in FIG. 12, a cap 220 can be provided that covers the injector engaging end 112 of the adapter 104 prior to use to help keep the adapter sterile. The cap 220 is removable to allow for coupling an injector to with the adaptor 200. FIG. 13 is a cross sectional view taken along ling XIV in FIG. 12. As illustrated, an insert 230 is positioned within the injector engaging end 112 of the adapter 104. The insert 230 is configured to allow for injectors of differing sizes to be coupled and engaged to the adapter 104. In some embodiments, for example, the interior dimensions of the injector engaging end 112 of the adapter 104 may be configured to receive, and generally may correspond in size to, a preselected jet injector type. The insert 230 may be removed for use of the adapter 104 with the jet injector. With the insert 230 in place, the insert can provide dimensions selected for receiving a syringe for reconstituting medicament. Generally, the insert 230 may include flanges 232 that may be inserted into engagement slots 170 of the adapter 104 to secure the insert relative to the adapter. These same slots 170 may be used for engaging a jet injector in place as it is being loaded (i.e., as it extracts liquid from a vial).

Figure 14:
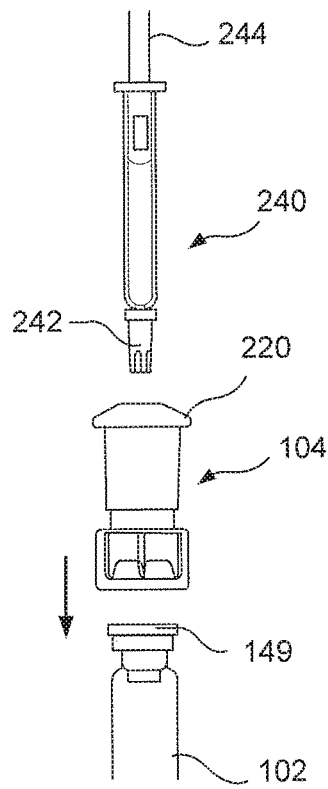
FIGS. 14-17 illustrate steps in an embodiment of a method of inserting liquid into the vial using the adapter.
Figure 15:
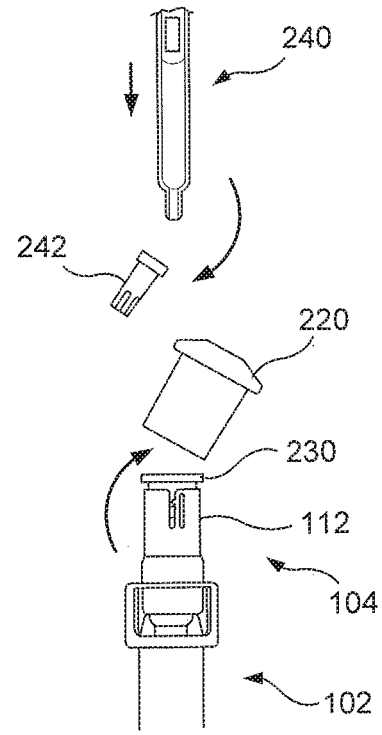
Figure 16:
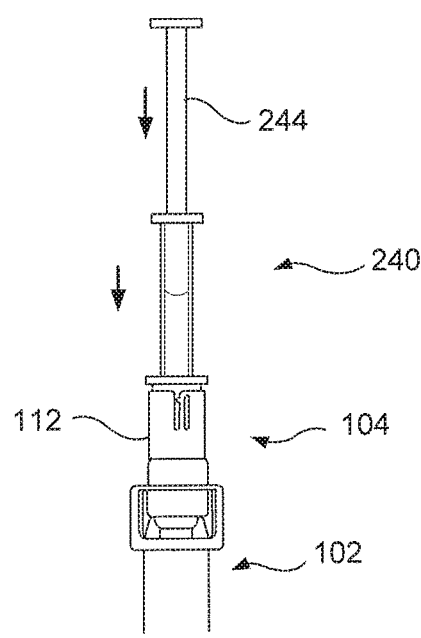
Figure 17:
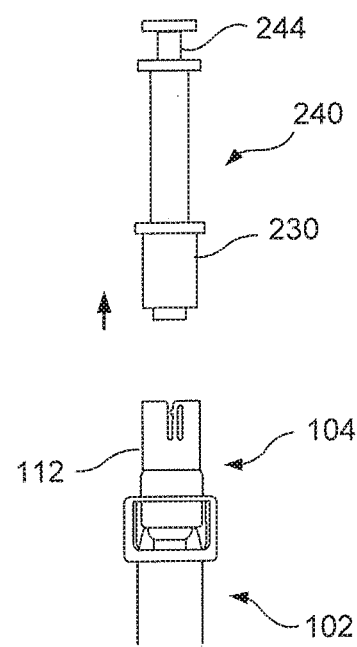

FIGS. 14-17 illustrate a process for reconstituting medicament using a syringe 240. In FIG. 14 each of the vial 102, the adapter 104 and the syringe 240 are shown as initially being separate from each other. The adapter 104 may be moved downward to engage the vial 102. In FIG. 15, the cap 220 is removed from the adapter 104 and a cap 242 is removed from the syringe 240. The syringe 240 engages the adapter 104 by entering the injector engaging end 112 of the adapter. Once the syringe 240 and the adapter 104 are joined together, a plunger 244 of the syringe 240 may be depressed to insert liquid into the vial, as shown in FIG. 16. Once the liquid from the syringe has been inserted into the vial 102, the syringe 240 may be removed from the adapter 104. As illustrated in FIG. 17, when the syringe is withdrawn from the injector engaging end 112 of the adapter 104, the insert 230 may be extracted from the adapter as well.

The facets 204 meet at a tip 210 and each facet joins with adjacent facets to form edges 212. The tip 210 is axially centered with respect to the spike 202. The edges 212 at the junction of the facets 204 may be used to cut through a rubber septum or stopper of a vial. Hence, the edges 212 are cutting edges. Furthermore, the apertures 206 are positioned between the edges 212 but do not interfere or disrupt the edges. As such, the edges 212 are disposed more radially outward than the interior portions of the facets 204 where the apertures 206 are positioned. The outward position of the edges 212 localizes the strain concentrations of the septum thereon and away from the apertures 206 as the spike 202 penetrates it.

Figure 18:
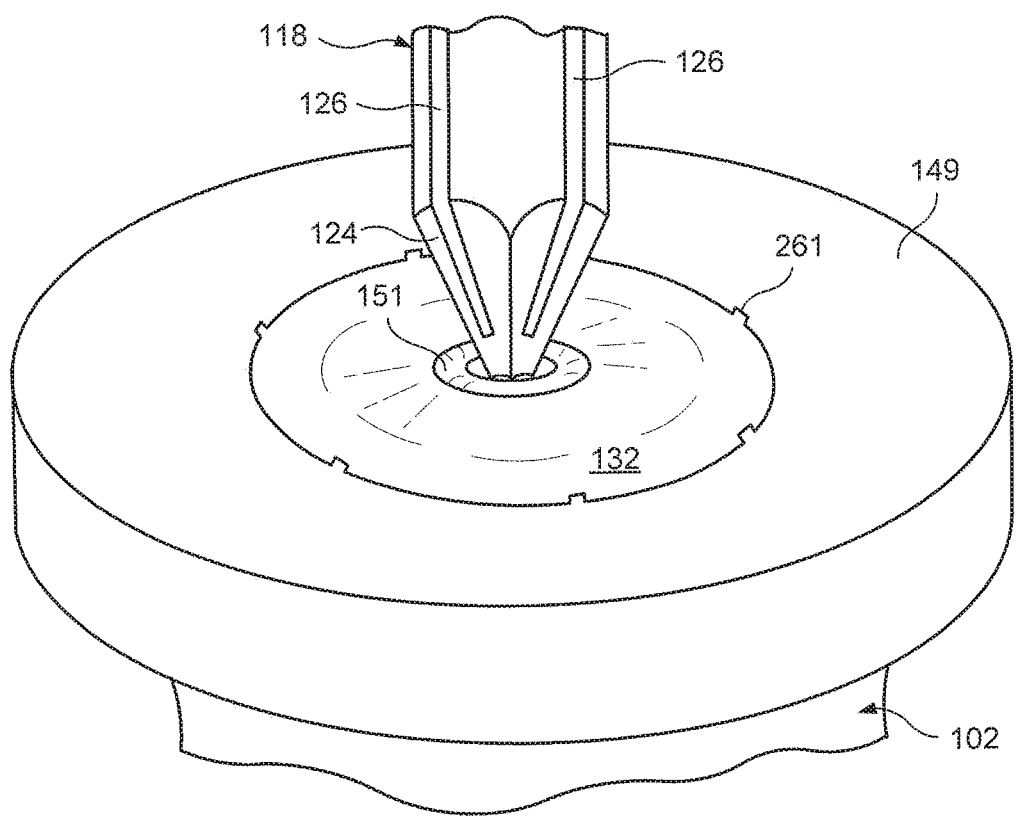
FIG. 18 is a perspective view of an embodiment of a spike penetrating a septum of a vial.
Figure 19:
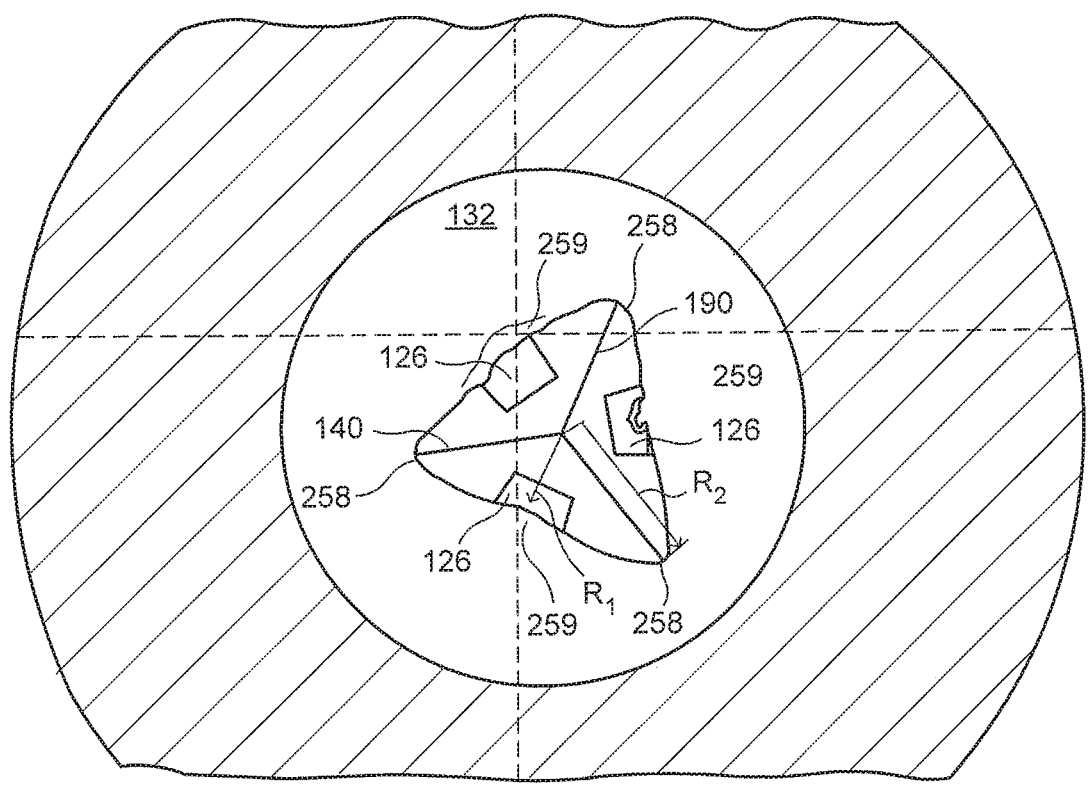
FIGS. 19 and 20 are axial views of the spike of FIG. 18 partially and completely, respectively, penetrating through the septum of a vial.
Figure 20:
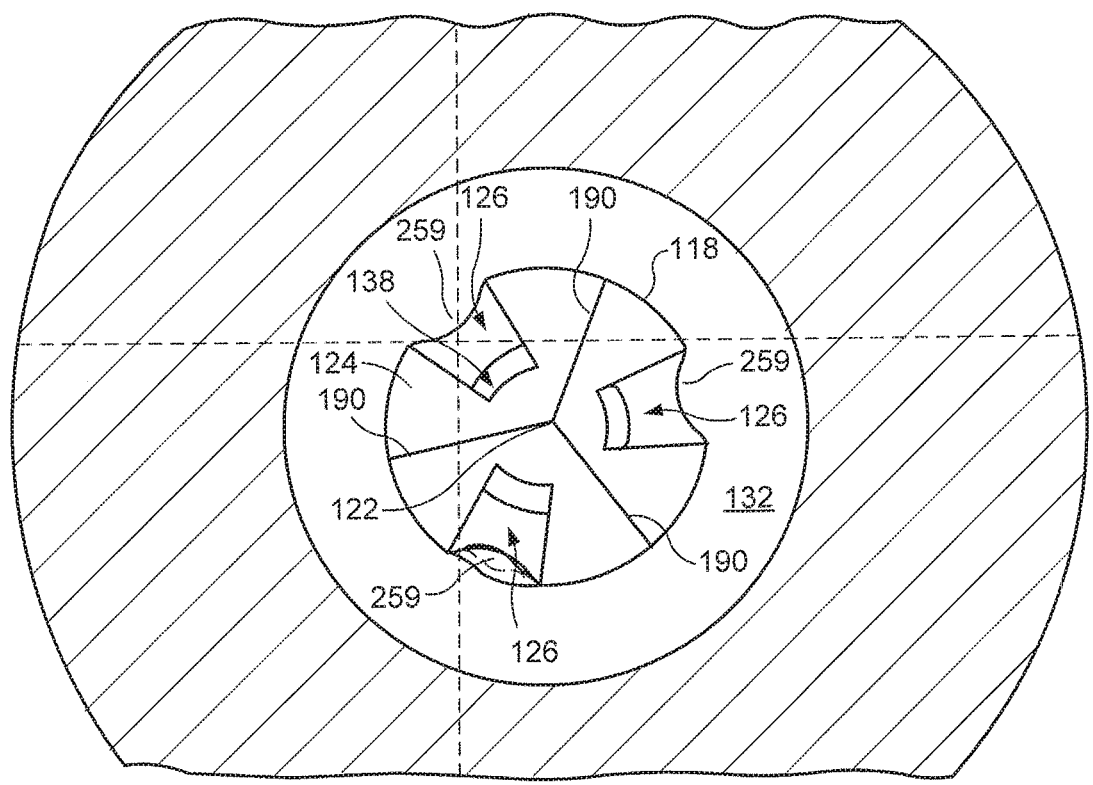

FIGS. 18-20 are images of the spike 118 penetrating the rubber stopper132 of the vial 102, for example when the adapter 104 is engaging the vial. In particular, FIG. 18 shows the spike 118 from outside the vial 102. The multiple facets 124 may be seen as having channel openings 126 that extend on the sidewall 128 of the shaft 129 of the spike 118. Additionally, the metal collar 149 may be seen. The tab of the metal collar has been removed to allow the spike access to the stopper 132 and remnants 261 of where the tab was connected to the collar 149 remain. The protrusion 151 of the stopper is also shown and serves as a target for the spike 118. The edges 190 at the junction between facets 124 serve as cutting edges as the spike 118 punctures the stopper 132.

FIG. 19 shows a view from within the vial as the spike 118 is pushed through the stopper 132. In some embodiments, tearing of the stopper 132 may occur upon insertion of the spike 118. The edges 190 are preferably sufficiently sharp to provide cutting through the elastomeric stopper 132 to facilitate penetration of the spike 118 therein. As the edges 190 extend radially further than the facet's 124 surfaces the pressure from the stopper 132 is concentrated at the edges. More specifically, stress concentrations from cutting, stretching, and/or tearing of the stopper are localized away from the openings 126 and instead are focused at the points 258 where the edges 190 are contacting the stopper. Thus, the channel openings 126 generally do not provide edges or points for cutting the stopper. This can help avoid coring of the stopper and minimize intrusion of the stopper into the openings 126. Preferably, the stopper 132 material will be pulled away from the channels 126 by the edges 190, and the stopper material that expands into the openings is minimized, such as at 259.

FIG. 20 shows the spike 118 fully inserted into the vial 102. As may be seen, the edges 190 are cleared from the stopper 132 and the channel openings 126 are exposed. Although not shown here, as the spike 118 is pushed through the stopper 132, the stopper is deflected slighted into the vial 132. As such, in a preferred embodiment, the distal end of the channel openings 126 are either flush with the stopper 132 or remain within the stopper so that substantially all of the liquid within the vial may be extracted into an injector, as discussed above.

Figure 21:
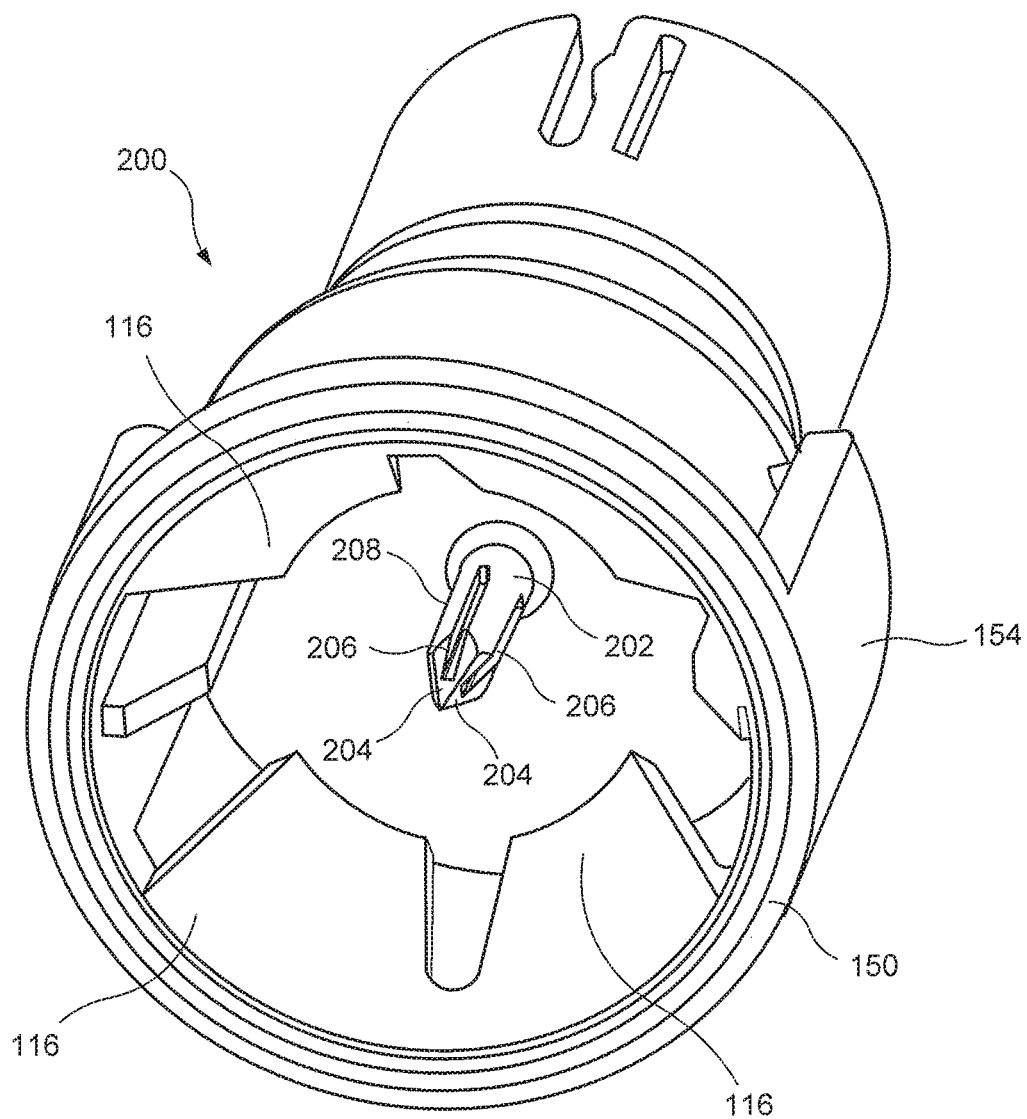
FIG. 21 illustrates a spike having four facets in accordance with and alternative embodiment.

FIG. 21 is a perspective view of another embodiment of a liquid-transfer adapter 200, which has a spike 202 with four facets 204. Each facet 204 may be similarly or differently sized, and preferably has a channel opening 206 that extends from within the face of the facet and onto the sidewall 208 of the spike 202. The opening 206 is in communication with a channel (not shown) within the spike 202 to provide liquid communication between two ends of the adapter 200.

All of the references specifically identified in the detailed description section of the present application are expressly incorporated herein in their entirety by reference thereto. The term "about," as used herein, should generally be understood to refer to both the corresponding number and a range of numbers. Moreover, all numerical ranges herein should be understood to include each whole integer within the range, and other embodiments can have other dimensions. Accordingly, the specific embodiments described herein should be understood as examples and not limiting the scope thereof.

While illustrative embodiments of the disclosure are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present disclosure.

What is claimed is:

1. A liquid-transfer adapter operatively interposable between an injector and a vial, comprising:
    an injector engaging portion configured for fluidly coupling to the injector;
    a vial coupling including a spike that has a spike axis and a tip portion configured for piercing a septum of the vial, the tip portion including plurality of facets that meet each other at one or more edges, at least one of the one or more edges being sloped with respect to the spike axis, the spike defining a channel extending therethrough in fluid communication with the injector engaging portion and including a channel opening defined in at least one of the facets and disposed without interrupting the edges;
    a body adjacent the injector engaging portion, the spike extending from the body;
    a collar coupled to the body by a support structure such that the collar is spaced from the body by a distance that is greater than a length of the spike, the collar comprising a continuous circumferential collar; and
    fingers having a proximal end and a distal end, the distal end coupled to the collar and extending inwardly and proximally toward the injector engaging portion, the fingers configured to couple the liquid-transfer adapter to the vial, wherein the proximal end comprises a free end.

2. The liquid-transfer adapter of claim 1, wherein the edges comprise junctions between the facets.

3. The liquid-transfer adapter of claim 1, wherein the edges comprise cutting surfaces configured for cutting the septum as the spike is pushed therethrough.

4. The liquid-transfer adapter of claim 1, wherein the tip portion comprises at least three facets.

5. The liquid-transfer adapter of claim 4, wherein the channel opening comprises a channel opening disposed in each of at least three of the facets.

6. The liquid-transfer adapter of claim 1 further comprising a seal disposed at the injector engaging portion configured for mating with the injector for maintaining liquid within the channel and injector.

7. The liquid-transfer adapter of claim 1, wherein the fingers comprise reflexed fingers configured for snapping to and retaining the liquid-transfer adapter engaged to the vial.

8. The liquid-transfer adapter of claim 1, wherein the channel openings are spaced circumferentially from the edges.

9. The liquid-transfer adapter of claim 1, wherein lateral edges of the channel openings are disposed radially inward compared to the edges.

10. The liquid-transfer adapter of claim 1, wherein lateral edges of the channel openings are disposed radially inward relative to the edges at any axial position.

11. The liquid-transfer adapter of claim 1, wherein the lateral edges of the channel openings are spaced from the edges sufficiently to minimize intrusion of the septum into the channel openings when the spike is pierced through the septum.

12. The liquid-transfer adapter of claim 1, wherein the channel openings are substantially centered circumferentially on the facets.

13. The liquid-transfer adapter of claim 1, wherein the injector engaging portion comprises dimensions suitable for coupling with a needle free injector.

14. The liquid-transfer adapter of claim 13, wherein a removable insert is removably coupled within the injector engaging portion for selectively configuring the injector engaging portion for engaging variously sized injectors.

15. The liquid-transfer adapter of claim 14, wherein the removable insert comprises dimensions suitable for coupling with a syringe having a first width, and with the insert removed, the injector engaging portion is configured for coupling to a jet injector having a second width that is larger than the first width.

16. The liquid-transfer adapter of claim 1, wherein:
    the spike comprises a shaft including a sidewall, the shaft extending from the tip towards the injector engaging portion; and
    the channel opening extends onto the sidewall of the shaft.

17. The liquid-transfer adapter of claim 1, wherein the edges meet at a point that is substantially axially centered.

18. The liquid-transfer adapter of claim 1, wherein the facets are substantially flat bevels.

19. The liquid transfer adapter of claim 1, wherein the support structure is one of a plurality of support structures, each of the plurality of support structures circumferentially spaced from another of the plurality of support structures.

20. The liquid transfer adapter of claim 1, wherein the fingers are configured to engage a lip of the vial.

21. The liquid transfer adapter of claim 16, wherein the channel opening is configured such that at least a portion of the channel opening is within the septum of the vial when the vial coupling is coupled to the vial.

22. A liquid-transfer adapter operatively interposable between an injector and a vial, comprising:

an injector engaging portion configured for fluidly coupling to the injector;
a vial coupling including a spike that has a spike axis and a tip portion configured for piercing a septum of the vial, the tip portion including a plurality of facets that meet each other at one or more edges, at least one of the one or more edges being sloped with respect to the spike axis, the spike defining a channel extending therethrough in fluid communication with the injector engaging and including a channel opening defined in at least one of the facets, wherein the channel openings are spaced circumferentially from the edges;
a body adjacent the injector engaging portion, the spike extending from the body;
a collar coupled to the body by a support structure such that the collar is spaced from the body by a distance that is greater than a length of the spike, wherein the collar comprises a continuous circumferential collar; and
fingers having a proximal end and a distal end, the distal end coupled to the collar and extending inwardly and proximally toward the injector engaging portion, the fingers configured to couple the liquid-transfer adapter to the vial, wherein the proximal end comprises a free end.

* * * * *